United States Patent
Ellingson et al.

(10) Patent No.: US 11,478,647 B2
(45) Date of Patent: *Oct. 25, 2022

(54) AUTOMATIC SELECTION OF PARAMETERS OF AN EXPOSURE MODE OF AN IMPLANTABLE MEDICAL DEVICE

(71) Applicant: Medtronic, Inc., Minneapolis, MN (US)

(72) Inventors: Michael L. Ellingson, St. Louis Park, MN (US); Hyun J. Yoon, Vadnais Heights, MN (US)

(73) Assignee: MEDTRONIC, INC., Minneapolis, MN (US)

(*) Notice: Subject to any disclaimer, the term of this patent is extended or adjusted under 35 U.S.C. 154(b) by 223 days.

This patent is subject to a terminal disclaimer.

(21) Appl. No.: 16/697,267

(22) Filed: Nov. 27, 2019

(65) Prior Publication Data

US 2020/0101298 A1    Apr. 2, 2020

Related U.S. Application Data

(60) Continuation of application No. 14/886,152, filed on Oct. 19, 2015, now Pat. No. 10,493,286, which is a (Continued)

(51) Int. Cl.
*A61N 1/37* (2006.01)
*A61N 1/372* (2006.01)
*A61N 1/368* (2006.01)

(52) U.S. Cl.
CPC ....... *A61N 1/3718* (2013.01); *A61N 1/37254* (2017.08); *A61N 1/3688* (2013.01)

(58) Field of Classification Search
CPC . A61N 1/3718; A61N 1/37252; A61N 1/3688
See application file for complete search history.

(56) References Cited

U.S. PATENT DOCUMENTS

| 5,722,998 A | 3/1998 | Prutchi et al. |
| 6,937,906 B2 | 8/2005 | Terry et al. |

(Continued)

FOREIGN PATENT DOCUMENTS

EP    1935450 A1    6/2008

OTHER PUBLICATIONS (PCT/US2010/031242) PCT Notification of Transmittal of the International Search Report and the Writter Opinion of the International Searching Authority, dated Jul. 1, 2010, 9 pages.

*Primary Examiner* — Alyssa M Alter
(74) *Attorney, Agent, or Firm* — Withers & Keys, LLC

(57) ABSTRACT

An implantable medical device (IMD) automatically determines at least a portion of the parameters and, in some instances all of the parameters, of an exposure operating mode based on stored information regarding sensed physiological events or therapy provided over a predetermined period of time. The IMD may configure itself to operate in accordance with the automatically determined parameters of the exposure operating mode in response to detecting a disruptive energy field. Alternatively, the IMD may provide the automatically determined parameters of the exposure operating mode to a physician as suggested or recommended parameters for the exposure operating mode. In other instances, the automatically determined parameters may be compared to parameters received manually via telemetry and, if differences exist or occur, a physician or patient may be notified and/or the manual parameters may be overridden by the automatically determined parameters.

24 Claims, 8 Drawing Sheets

Related U.S. Application Data division of application No. 12/569,101, filed on Sep. 29, 2009, now Pat. No. 9,174,058.

(56) References Cited

U.S. PATENT DOCUMENTS

| | | |
|---|---|---|
| 7,212,863 B2 | 5/2007 | Strandberg |
| 7,561,915 B1 | 7/2009 | Cooke et al. |
| 2004/0254614 A1 | 12/2004 | Spinelli et al. |
| 2005/0096708 A1 | 5/2005 | Seim et al. |
| 2005/0149126 A1 | 7/2005 | Libbus |
| 2006/0167496 A1* | 7/2006 | Nelson ............... A61N 1/37235 607/2 |
| 2006/0293591 A1 | 12/2006 | Wahlstrand et al. |
| 2007/0265662 A1 | 11/2007 | Ufford |
| 2008/0154342 A1 | 6/2008 | Digby et al. |
| 2009/0157146 A1 | 6/2009 | Linder et al. |

\* cited by examiner

AUTOMATIC SELECTION OF PARAMETERS OF AN EXPOSURE MODE OF AN IMPLANTABLE MEDICAL DEVICE

CROSS REFERENCE TO RELATED APPLICATIONS

This application is a Continuation of U.S. patent application Ser. No. 14/886,152, (U.S. Publication No. 2016/0038744), filed Oct. 19, 2015, which was a Division of U.S. patent application Ser. No. 12/569,101, now U.S. Pat. No. 9,174,058, filed Sep. 29, 2009, the content of both of which are incorporated herein by reference in their entirety.

TECHNICAL FIELD

The disclosure relates generally to implantable medical devices and, in particular, to operation of an implantable medical device when exposed to a disruptive energy field.

BACKGROUND

A wide variety of implantable medical devices (IMDs) that deliver a therapy to or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in improper operation of the IMD, damage to the IMD and/or damage to tissue adjacent to portions of the IMD. The IMD may be exposed to the disruptive energy field for any of a number of reasons. For example, one or more medical procedures may need to be performed on the patient within which the IMD is implanted for purposes of diagnostics or therapy. For example, the patient may need to have a magnetic resonance imaging (MRI) scan, computed tomography (CT) scan, electrocautery, diathermy or other medical procedure that produces a magnetic field, electromagnetic field, electric field or other disruptive energy field.

The disruptive energy field may induce energy on one or more of the implantable leads coupled to the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy when it is not desired or withholding therapy when it is desired. In other instances, the induced energy on the leads may result in stimulation or heating of the tissue and/or nerve site adjacent to the electrodes of the leads or adjacent to the housing of the IMD. Such heating may result in thermal damage to the tissue, thus compromising pacing and sensing thresholds at the site.

SUMMARY

In general, this disclosure relates to operation of an implantable medical device (IMD) in a disruptive energy field. In particular, this disclosure describes techniques for automatically determining at least a portion of the parameters and, in some instances all of the parameters, of an exposure operating mode based on stored information regarding sensed physiological events or therapy provided over a predetermined period of time. For example, the IMD may analyze parameters of therapy, if any, provided over the predetermined period of time, such as pacing modes in which the device operated over the predetermined period of time, amplitudes of the therapy energy delivered during the predetermined period of time, pulse widths of the therapy energy delivered during the predetermined period of time, heart rate during the predetermined period of time, or the like. Based on this analysis, the device may determine one or more parameters of the exposure operating mode, such as a pacing mode and amplitude, pulse width, and/or rate of the therapy energy delivered during the exposure operating mode. The IMD may automatically determine the parameters periodically or non-periodically, e.g., in response to some input.

The IMD may configure itself to operate in accordance with the automatically determined parameters of the exposure operating mode in response to detecting a disruptive energy field. Alternatively, the IMD may provide the automatically determined parameters of the exposure operating mode to a physician as suggested or recommended parameters for the exposure operating mode. In other instances, the automatically determined parameters may be compared to parameters received manually via telemetry and, if any significant differences exist or occur, a physician or patient may be notified and/or the manual parameters may be overridden by the automatically determined parameters.

In one example, this disclosure is directed to an implantable medical device comprising a memory and a processor that automatically determines one or more parameters of an exposure operating mode based on information stored in the memory related to sensed physiological events or therapy provided over a predetermined period of time and switches operation of the implantable medical device from parameters of a current operating mode to the one or more automatically determined parameters of the exposure operating mode.

In another example, this disclosure is directed to a method comprising automatically determining, with an implantable medical device, one or more parameters of an exposure operating mode based on stored information related to sensed physiological events or therapy provided over a predetermined period of time and switching operation of the implantable medical device from parameters of a current operating mode to the one or more automatically determined parameters of the exposure operating mode.

In a further example, this disclosure is directed to an implantable medical device comprising means for automatically determining one or more parameters of an exposure operating mode based on stored information related to sensed physiological events or therapy provided over a predetermined period of time and means for switching operation of the implantable medical device from parameters of a current operating mode to the one or more automatically determined parameters of the exposure operating mode.

In another example, this disclosure is directed to a computer-readable medium comprising instructions that, when executed, cause an implantable medical device to automatically determine one or more parameters of an exposure operating mode based on stored information related to sensed physiological events or therapy provided over a predetermined period of time and switch operation of the implantable medical device from parameters of a current operating mode to the one or more automatically determined parameters of the exposure operating mode.

The details of one or more examples are set forth in the accompanying drawings and the description below. Other features, objects, and advantages will be apparent from the description and drawings, and from the statements provided below.

DETAILED DESCRIPTION

Figure 1:
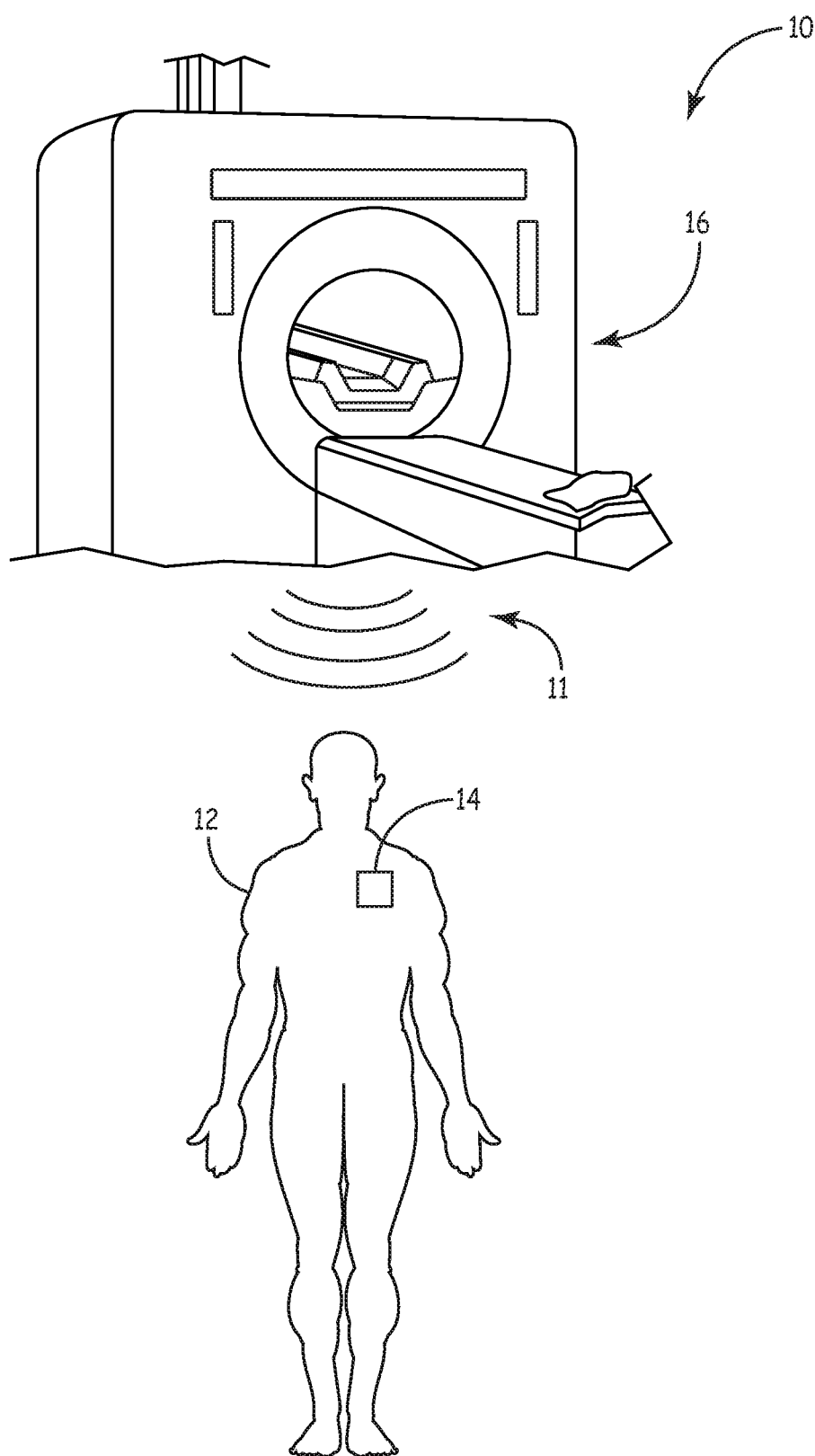
FIG. 1 is a conceptual diagram illustrating an environment in which an implantable medical device (IMD) is exposed to a disruptive energy field.

FIG. 1 is a conceptual diagram illustrating an environment 10 in which an implantable medical device (IMD) 14 is exposed to a disruptive energy field 11. IMD 14 is implanted within patient 12 to provide therapy to or to monitor a physiological condition of patient 12. The techniques, however, are not limited to devices implanted within patient 12. For example, the techniques may be used in conjunction with an external medical device that is adversely affected by disruptive energy field 11.

IMD 14 may be any of a variety of devices that provide therapy to patient 12, monitor a condition of patient 12, or both. For example, IMD 14 may be a device that provides electrical stimulation therapy via one or more implantable leads that include one or more electrodes (not shown in FIG. 1). In some instances, IMD 14 may be a device that provides electrical stimulation therapy in the form of cardiac rhythm management therapy to a heart of patient 12 via leads implanted within one or more atria and/or ventricles of the heart. The cardiac rhythm management therapy delivered by IMD 14 may include pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarization of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like. In some instances, IMD 14 may be used solely for monitoring a condition of patient 12. In other words, IMD 14 may not provide therapy to patient 12, but simply sense a physiological or biological condition of patient 12.

In yet other instances, IMD 14 may be a device that delivers a drug or therapeutic agent to patient 12 via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Environment 10 includes an energy source that generates disruptive energy field 11 to which IMD 14 is exposed. In the example illustrated in FIG. 1, the energy source is an MRI scanner 16. Although the techniques of this disclosure are described with respect to disruptive energy field 11 generated by MRI scanner 16, the techniques may be used to control operation of IMD 14 within environments in which other types of disruptive energy fields are present. For example, IMD 14 may operate in accordance with the techniques of this disclosure in environments in which disruptive energy field 11 is generated by a CT scanner, X-ray machine, electrocautery device, diathermy device, ablation device, radiation therapy device, electrical therapy device, magnetic therapy device, RFID security gate, or any other environment with devices that radiate energy to produce magnetic, electromagnetic, electric fields or other disruptive energy fields.

MRI scanner 16 uses magnetic and radio frequency (RF) fields to produce images of body structures for diagnosing injuries, diseases and/or disorders. In particular, MRI scanner 16 generates a static magnetic field, gradient magnetic fields and/or RF fields. The static magnetic field is a non-varying magnetic field that is typically always present around MRI scanner 16 whether or not an MRI scan is in progress. Gradient magnetic fields are pulsed magnetic fields that are typically only present while the MRI scan is in progress. RF fields are pulsed RF fields that are also typically only present while the MRI scan is in progress.

Some or all of the various types of fields produced by MRI scanner 16 may interfere with operation of IMD 14. In other words, one or more of the various types of fields produced by MRI scanner 16 may make up disruptive energy field 11. For example, the gradient magnetic and RF fields produced by MRI scanner 16 may induce energy on one or more of the implantable leads coupled to IMD 14. In some instances, IMD 14 inappropriately detects the induced energy on the leads as physiological signals, which may in turn cause IMD 14 to deliver undesired therapy or withhold desired therapy. In other instances, the induced energy on the leads result in IMD 14 not detecting physiological signals that are actually present, which may again result in IMD 14 delivering undesired therapy or withholding desired therapy. The induced energy on the leads may be delivered to the tissue of patient 12 resulting in stimulation or heating of the tissue and/or nerve site adjacent to electrodes of the leads. Such heating may cause thermal damage to the tissue adjacent the electrodes, possibly compromising pacing and sensing thresholds at the site. In yet other instances, the induced energy may cause damage to one or more components of IMD 14.

To reduce the undesirable effects of disruptive energy field 11, IMD 14 is capable of operating in a mode that is less susceptible to undesirable operation during exposure to disruptive energy field 11, referred to herein as the "exposure mode" or "exposure operating mode." Prior to being exposed or upon being exposed to disruptive energy field 11, IMD 14 is configured from a normal operating mode (e.g., the current operating mode) to the exposure operating mode. IMD 14 may be configured from the normal mode to the exposure mode automatically, e.g., in response to detection of disruptive energy field 11, or manually, e.g., via an external programming device.

In the normal operating mode, IMD 14 operates in accordance with all desired functionality using settings programmed by a physician, clinician or other user. When operating in the normal operating mode, IMD 14 may perform functions in a manner that does not specifically account for the presence of strong disruptive energy fields. The normal mode may correspond with the operating mode that a physician or other user feels provides a most efficacious therapy for patient 12. While operating in accordance with the normal operating mode, IMD 14 may sense physiological events, deliver a number of different therapies, and log collected data.

In the exposure mode, however, IMD 14 may perform functions in a manner that specifically accounts for the presence of strong disruptive energy fields. While operating in the exposure mode, IMD 14 may be configured to operate with different functionality than when operating in the normal operating mode. IMD 14 may, in some instances, be configured to operate with reduced functionality. In other words, when configured to operate in the exposure mode, IMD 14 may have only a subset of the functionality of the normal operating mode. For example, IMD 14 may not provide sensing, not deliver therapy, delivery only a subset of possible therapies, not log collected data or the like. In other instances, IMD 14 may be operating with approximately the same functionality or even increased functionality in the exposure mode. For example, IMD 14 may use a different sensor or algorithm to detect cardiac activity of the heart of patient 12, such as pressure sensor measurements rather than electrical activity of the heart. In either case, it is desirable that IMD 14 be reconfigured from the exposure operating mode to the normal operating mode as soon as safely possible after exiting from environment 10.

In accordance with one aspect of this disclosure, IMD 14 automatically determines at least a portion of the parameters and, in some instances all of the parameters, of the exposure operating mode based on stored information regarding sensed physiological events or therapy provided over a predetermined period of time. For example, IMD 14 may analyze parameters of therapy, if any, provided over the predetermined period of time, such as pacing modes in which the device operated over the predetermined period of time, percentage of time during which therapy is provided, amplitudes of the therapy energy delivered during the predetermined period of time, pulse widths of the therapy energy delivered during the predetermined period of time, heart rate during the predetermined period of time, or the like. Based on this analysis, the device may determine one or more parameters of the exposure operating mode, such as a pacing mode and amplitude, pulse width, and/or rate of the therapy energy delivered during the exposure operating mode. IMD 14 may automatically determine the parameters periodically or non-periodically, e.g., in response to some input.

IMD 14 stores the automatically determined parameters of the exposure operating mode and uses at least a portion of the parameters when it is configured into the exposure operating mode. In one instance, IMD 14 may configure itself to operate in accordance with the automatically determined parameters in response to detecting disruptive energy field 11, which may in one example be the static magnetic field of MRI scanner 16, the gradient magnetic fields of MRI scanner 16, or the RF fields of MRI scanner 16. In this case, IMD 14 may be a fully automated MR Conditional or MR Safe device that does not require any manual programming of the exposure operating mode parameters. This may reduce the service burden on the patient, physician, technician, clinician or other user involved in the process.

In another example, IMD 14 may receive, e.g., via telemetry, parameters for the exposure operating mode from a physician, clinician, or other person. The IMD may continue to automatically determine parameters of the exposure operating mode and compare the automatically determined parameters with the parameters that were manually programmed. If there are differences between the automatically determined parameters and the manually programmed parameters, IMD 14 may initiate an alert to patient 12 and/or a physician notifying them that the automatically determined parameters differ from the manually programmed parameters. In some instances, IMD 14 may only notify patient 12 and/or the physician if the differences are determined to be significant. Whether a difference is determined to be significant may be determined differently depending on the circumstances of a particular patient 12, the physician treating the patient or the like. Alternatively or additionally, IMD 14 may provide the automatically determined parameters to the physician or clinician at the time of the manual programming. In other words, IMD 14 may suggest appropriate parameters for the exposure operating mode. The physician, clinician or other user may accept the suggested parameters or adjust one or more of the suggested parameters. In the instances in which manually programming is involved, IMD 14 may enter and exit the exposure operating mode at the time of manual programming or automatically upon detecting disruptive energy field 11 as will be described in further detail.

By automatically determining the parameters of the exposure operating mode, IMD 14 may automatically configure itself to be MR Conditional or MR Safe without requiring manual programming by a physician, clinician or other person. Moreover, IMD 14 continues to update the parameters of the exposure operating mode until just before exposure to disruptive energy field 11. As such, automatically determining the parameters of the exposure operating mode may provide an added safety mechanism in case the condition of the patient changes from the time between the manual programming of the parameters of the exposure operating mode and the MRI scan.

Although described with respect to a medical environment that generates disruptive energy fields, the techniques of this disclosure may be used to operate IMD 14 within non-medical environments that include disruptive energy fields. Additionally, the techniques of this disclosure may also be used to operate IMD 14 within environments that produce disruptive energy fields that are intermittent in nature.

Figure 2:
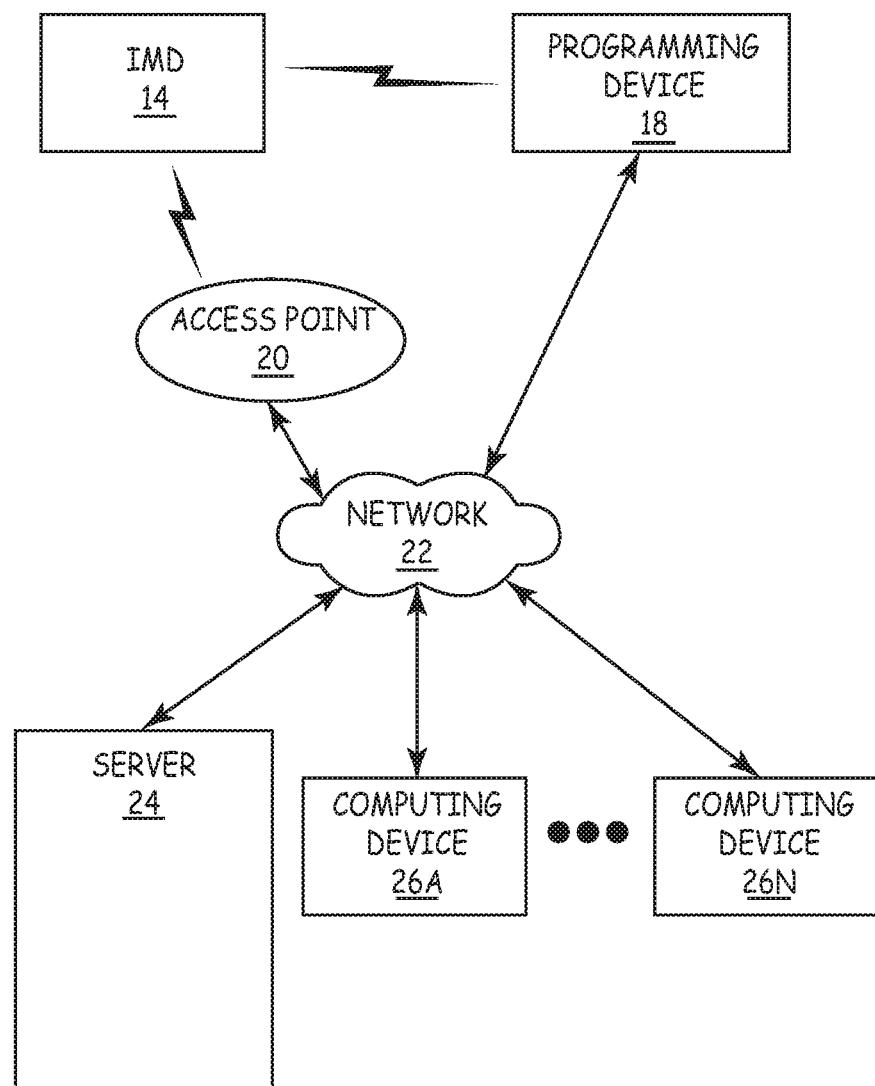
FIG. 2 is a block diagram illustrating an example system that includes an IMD, a programming device, an access point, a server and one or more computing devices interconnected, and able to communicate with each other, through a network.

FIG. 2 is a block diagram illustrating an example system that includes IMD 14, a programming device 18, an access point 20, a network 22, a server 24 and one or more computing devices 26A-26N. In the example of FIG. 2, programming device 18, access point 20, server 24 and computing devices 26 are interconnected, and able to communicate with each other, through network 22. Programming device 18, access point 20, server 24, and computing devices 26A-26N may each include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

Programming device 18 may be a dedicated hardware device with dedicated software for programming of IMD 14. Alternatively, programming device 18 may be an off-the-shelf computing device running an application that enables programming device 18 to program IMD 14. In some examples, programming device 18 may be a handheld computing device or a computer workstation. Programming device 18 may, in some instances, include a programming head that may be placed proximate to the patient's body near the implant site of IMD 14 in order to improve the quality or security of communication between IMD 14 and programming device 18. Programming device 18 may include a user interface that receives input from the user and/or displays data to the user.

Programming device 18 may communicate with IMD 14 via wireless communication using any techniques known in the art. Examples of communication techniques may include, for example, magnetic telemetry, low frequency telemetry or radio frequency (RF) telemetry, but other techniques are also contemplated. In some instances, programming device 18 and IMD 14 may communicate in the 402-405 MHz frequency band in accordance with the Medical Implant Communications Service (MICS) frequency band regulation, in the 401-402 MHz or 405-406 MHz frequency bands in accordance with the Medical External Data Service (MEDS) band regulations, in the unlicensed industrial, scientific and medical (ISM) band, or other frequency band.

A user, such as a physician, technician, clinician or patient, may interact with a programming device 18 to communicate with IMD 14. For example, the user may interact with programming device 18 to retrieve physiological or diagnostic information or history of therapies delivered from IMD 14. In the case of a cardiac implantable medical device, for instance, the user may use programming device 18 to retrieve information from IMD 14 regarding the rhythm of the heart of patient 12, trends therein over time, or cardiac arrhythmia episodes. As another example, the user may use programming device 18 to retrieve information from IMD 14 regarding other sensed physiological parameters of patient 12, such as electrical depolarization/repolarization signals from the heart (referred to as an "electrogram" or EGM), intracardiac or intravascular pressure, activity, posture, respiration or thoracic impedance. As another example, the user may use programming device 18 to retrieve information from IMD 14 regarding the performance or integrity of IMD 14 or other components of therapy system 30, such as leads or a power source of IMD 14.

The user may also interact with programming device 18 to program IMD 14, e.g., select values for operational parameters of IMD 14. For electrical stimulation therapies, for example, the user may interact with programming device 18 to program a therapy progression, select an electrode or combination of electrodes of leads 34 and 36 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

In some instances, a user interacts with programming device 18 to program IMD 14 into the exposure mode prior to patient 12 undergoing a medical procedure in which IMD 14 will be exposed to a disruptive energy field 11, e.g., before undergoing an MRI scan. In accordance with one aspect of this disclosure, IMD 14 may transmit automatically generated parameters suggested for the exposure operating mode to programming device 18 for presentation to the user. The user may view the suggested parameters automatically determined by IMD 14 and either accept the suggested parameters or change one or more of the suggested parameters. The device may then be programmed into the exposure mode using the parameters at that time or at a later time (e.g., in response to detecting the disruptive energy field 11).

The user may also reprogram IMD 14 from the exposure mode to a normal mode after the MRI scan is finished. Often times, an individual performing the MRI scan is not familiar with programming implanted devices. As such, a technician familiar with programming implanted devices needs to be present before and after the medical procedure, the MRI scan in this case. This is often burdensome as the medical procedure may take several hours. As such, IMD 14 may, in other instances, automatically reconfigure itself from the exposure operating mode to the normal operating mode. In other words, IMD 14 may revert to the normal operating mode without the technician using programming device 18 to manually reprogram IMD 14.

IMD 14 may communicate with programming device 18 via a first wireless connection and communicate with access point 20 via a second wireless connection. Programming device 18 and/or access point 20 may connect to network 22 via any of a variety of wired or wireless connections, such as telephone dial-up, digital subscriber line (DSL), cable modem connection, Infrared Data Association (IrDA), Bluetooth, IEEE 802.11, General Packet Radio Service (GPRS) or the like. As such, programming device 18 and access point 20 may forward data from IMD 14 to any other device connected to network 22.

In some embodiments, access point 20 may be co-located with patient 14 and may comprise one or more programming units and/or computing devices (e.g., one or more monitoring units) that may perform various functions and operations described herein. For example, access point 20 may include a home-monitoring unit that is co-located with patient 14 and that may monitor the activity of IMD 14. In some embodiments, server 24 or computing devices 26 may control or perform any of the various functions or operations described herein, e.g., view or change the automatically determined parameters of the exposure operating mode of IMD 14. In one aspect of this disclosure, IMD 14 may initially be manually programmed with parameters for the exposure operating mode. IMD 14 may, however, continue to automatically determine parameters for the exposure operating mode, e.g., on a periodic basis, after the manual programming. IMD 14 may compare the automatically generated parameters with the manually programmed parameters and, if there are any differences, IMD 14 may generate an alert for the physician indicating the difference. For example, IMD 14 may send an alert to server 24 or one or more of computing devices 26A-26N via access point 20 and network 22. Alternatively, the patient may be notified that he/she may need to revisit the physician prior to the MRI scan to have the exposure operating mode updated. IMD 14 may, in addition to or instead of the alert, override the manually programmed parameters with the automatically generated parameters either automatically or in response to a signal from a physician sent remotely via network 22. IMD 14 may, in some instances, only send the alert if the difference(s) is determined to be significant. Whether a difference is determined to be significant may be determined differently depending on the circumstances of a particular patient 12, the physician treating the patient or the like.

In some cases, server 24 may be configured to provide a secure storage site for archival of sensing integrity information that has been collected from IMD 14 and/or programming device 18. In some cases, programming device 18 or server 24 may assemble information, such as the automatically determined parameters of the exposure operating mode, in web pages or other documents for viewing by trained professionals, such as clinicians, via viewing terminals associated with computing devices 26. The system of FIG. 2 may be implemented, in some aspects, with general network technology and functionality similar to that provided by the Medtronic CareLink® Network developed by Medtronic, Inc., of Minneapolis, Minn.

Figure 3:
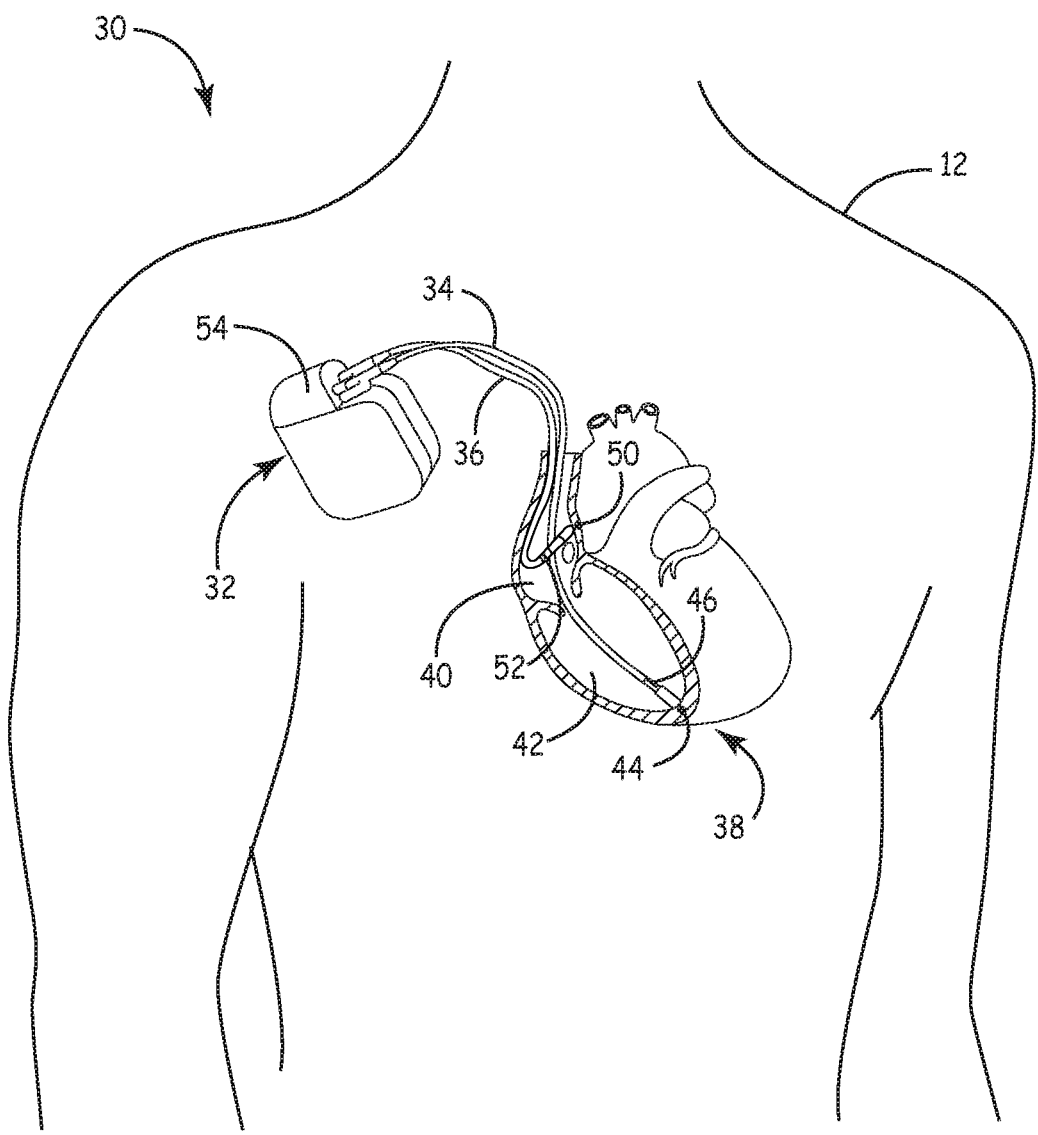
FIG. 3 is a conceptual diagram illustrating an example therapy system that may be used to provide therapy to patient.

FIG. 3 is a conceptual diagram illustrating an example therapy system 30 that may be used to provide therapy to patient 12. Therapy system 30 includes an IMD 32 and leads 34 and 36 that extend from IMD 32. IMD 32 may, for example, correspond to IMD 14 of FIG. 1 and FIG. 2.

In the example illustrated in FIG. 3, IMD 32 is an implantable cardiac device that senses electrical activity of a heart 38 of patient 12 and/or provides electrical stimulation therapy to heart 38 of patient 12. The electrical stimulation therapy to heart 38, sometimes referred to as cardiac rhythm management therapy, may include pacing, cardioversion, defibrillation and/or cardiac resynchronization therapy (CRT). The combinations of cardiac therapies provided may be dependent on a condition of patient 12. In some instances, IMD 32 may provide no therapy to patient 12, but instead provide only sensing of electrical activity or other variable of heart 30, such as in the case of an implantable loop recorder.

In the illustrated example, lead 34 is a right ventricular (RV) lead that extends through one or more veins (not shown), the superior vena cava (not shown), and right atrium 40, and into right ventricle 42 of heart 38. Lead 34 includes electrodes 44 and 46 located along a distal end of lead 34. In the illustrated example, lead 36 is right atrial (RA) lead that extends through one or more veins and the superior vena cava, and into the right atrium 40 of heart 38. Lead 36 includes electrodes 50 and 52 located along a distal end of lead 36.

Electrodes 44 and 50 may take the form of extendable helix tip electrodes mounted retractably within an insulative electrode head (not shown) of respective leads 34 and 36. Electrodes 46 and 52 may take the form of ring electrodes. In other embodiments, electrodes 44, 46, 50 and 52 may be other types of electrodes. For example, electrodes 44, 46, 50 and 52 may all be ring electrodes located along the distal end of the associated lead 34 or 36. Additionally, either or both of leads 34 and 36 may include more than two electrodes or only a single electrode.

Each of the electrodes 44, 46, 50 and 52 may be electrically coupled to a respective conductor within the body of its associated lead 34 and 36. The respective conductors may extend from the distal end of the lead to the proximal end of the lead and couple to circuitry of IMD 32. For example, leads 34 and 36 may be electrically coupled to a stimulation module, a sensing module, or other modules of IMD 32 via connector block 54. In some examples, proximal ends of leads 34 and 36 may include electrical contacts that electrically couple to respective electrical contacts within connector block 54. In addition, in some examples, leads 34 and 36 may be mechanically coupled to connector block 54 with the aid of set screws, connection pins or another suitable mechanical coupling mechanism.

When IMD 32 is capable of delivering electrical stimulation therapy, IMD 32 delivers the therapy (e.g., pacing pulses) to heart 38 via any combination of electrodes 44, 46, 50 and 52 to cause depolarization of cardiac tissue of heart 14. For example, IMD 32 may deliver bipolar pacing pulses to right atrium 40 via electrodes 50 and 52 of lead 36 and/or may deliver bipolar pacing pulses to right ventricle 42 via electrodes 44 and 46 of lead 34. In another example, IMD 32 may deliver unipolar pacing pulses to atrium 40 and ventricle 42 using a housing electrode (not shown) in conjunction with one of electrodes 44, 46, 50 and 52. The housing electrode may be formed integrally with an outer surface of the hermetically-sealed housing of IMD 32 or otherwise coupled to the housing. In some examples, the housing electrode is defined by an uninsulated portion of an outward facing portion of the housing of IMD 32.

Electrodes 44, 46, 50 and 52 may also sense electrical signals attendant to the depolarization and repolarization of heart 30. The electrical signals are conducted to IMD 32 via one or more conductors of respective leads 34 and 36. IMD 32 may use any combinations of the electrodes 44, 46, 50, 52 or the housing electrode for unipolar or bipolar sensing. As such, the configurations of electrodes used by IMD 32 for sensing and pacing may be unipolar or bipolar depending on the application. IMD 32 may analyze the sensed signals to monitor a rhythm of heart 38 or detect an arrhythmia of heart 38, e.g., tachycardia, bradycardia, fibrillation or the like. In some instances, IMD 32 provides pacing pulses (or other therapy) to heart 38 based on the cardiac signals sensed within heart 38. In other words, pacing may be responsive to the sensed events.

As described above, exposure of an implantable medical device, such as IMD 32 to a disruptive energy field 11 (FIG. 1) may result in undesirable operation. For example, gradient magnetic and RF fields produced by MRI scanner 16 (FIG. 1) may induce energy on one or more of electrodes 44, 46, 50 and 52 of respective ones of implantable leads 34 and 36 or on the housing electrode. In some instances, IMD 32 inappropriately detects the induced energy on electrodes 44, 46, 50 and 52 as physiological signals, which may in turn cause IMD 32 to deliver undesired therapy or withhold desired therapy. In other instances, the induced energy on electrodes 44, 46, 50 and 52 result in IMD 32 not detecting physiological signals that are actually present, which may again result in IMD 32 delivering undesired therapy or withholding desired therapy. In further instances, the induced energy on electrodes 44, 46, 50 and 52 result in stimulation or heating of the tissue and/or nerve site adjacent to electrodes 44, 46, 50 and 52 or the housing of IMD 32. Such heating may result in thermal damage to the tissue adjacent the electrodes, possibly compromising pacing and sensing thresholds at the site. Yet another possible adverse affect of disruptive energy field 11 is damage to circuitry within IMD 32.

Configuring IMD 32 into an exposure operating mode may reduce, and possibly eliminate, the undesirable operation of IMD 32. As such, IMD 32 may be configured to operate in the exposure operating mode prior to or immediately subsequent to entering the environment in which the disruptive energy field 11 is present. In accordance with one aspect of this disclosure, IMD 32 automatically determines at least a portion of the parameters and, in some instances all of the parameters, of the exposure operating mode based on stored information regarding sensed physiological events or provided therapy prior to entering the environment with disruptive energy field 11. At least a portion of these automatically determined parameters are used in configuring IMD 32 into the exposure operating mode as described in further detail in this disclosure. IMD 32 may, for example, automatically configure itself into the exposure operating mode using the automatically determined parameters. In another example, the automatically determined parameters may be provided to a user (e.g., physician) as a suggested set of parameters for the exposure operating mode and the user accepts the parameters as is or modifies one or more of the parameters to manually configure IMD 32 into the exposure operating mode. In a further example, IMD 32 may update or override manually programmed parameters with parameters that are automatically determined subsequent to the manual programming.

The configuration of therapy system 30 illustrated in FIG. 3 is merely an example. In other examples, therapy system 30 may include more or fewer leads extending from IMD 32. For example, IMD 32 may be coupled to three leads, e.g., a third lead implanted within a left ventricle of heart 30. In another example, IMD 32 may be coupled to a single lead that is implanted within either an atrium or ventricle of heart 38. As such, IMD 32 may be used for single chamber or multi-chamber cardiac rhythm management therapy.

In addition to more or fewer leads, each of the leads may include more or fewer electrodes. In instances in which IMD 32 is used for therapy other than pacing, e.g., defibrillation or cardioversion, the leads may include elongated electrodes, which may, in some instances, take the form of a coil. IMD 32 may deliver defibrillation or cardioversion shocks to heart 38 via any combination of the elongated electrodes and housing electrode. As another example, therapy system 30 may include leads with a plurality of ring electrodes, e.g., as used in some implantable neurostimulators.

In still other examples, a therapy system may include epicardial leads and/or patch electrodes instead of or in addition to the transvenous leads 34 and 36 illustrated in FIG. 3. Further, IMD 32 need not be implanted within patient 12. In examples in which IMD 32 is not implanted in patient 12, IMD 32 may deliver electrical stimulation therapy to heart 38 via percutaneous leads that extend through the skin of patient 12 to a variety of positions within or outside of heart 38.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 4:
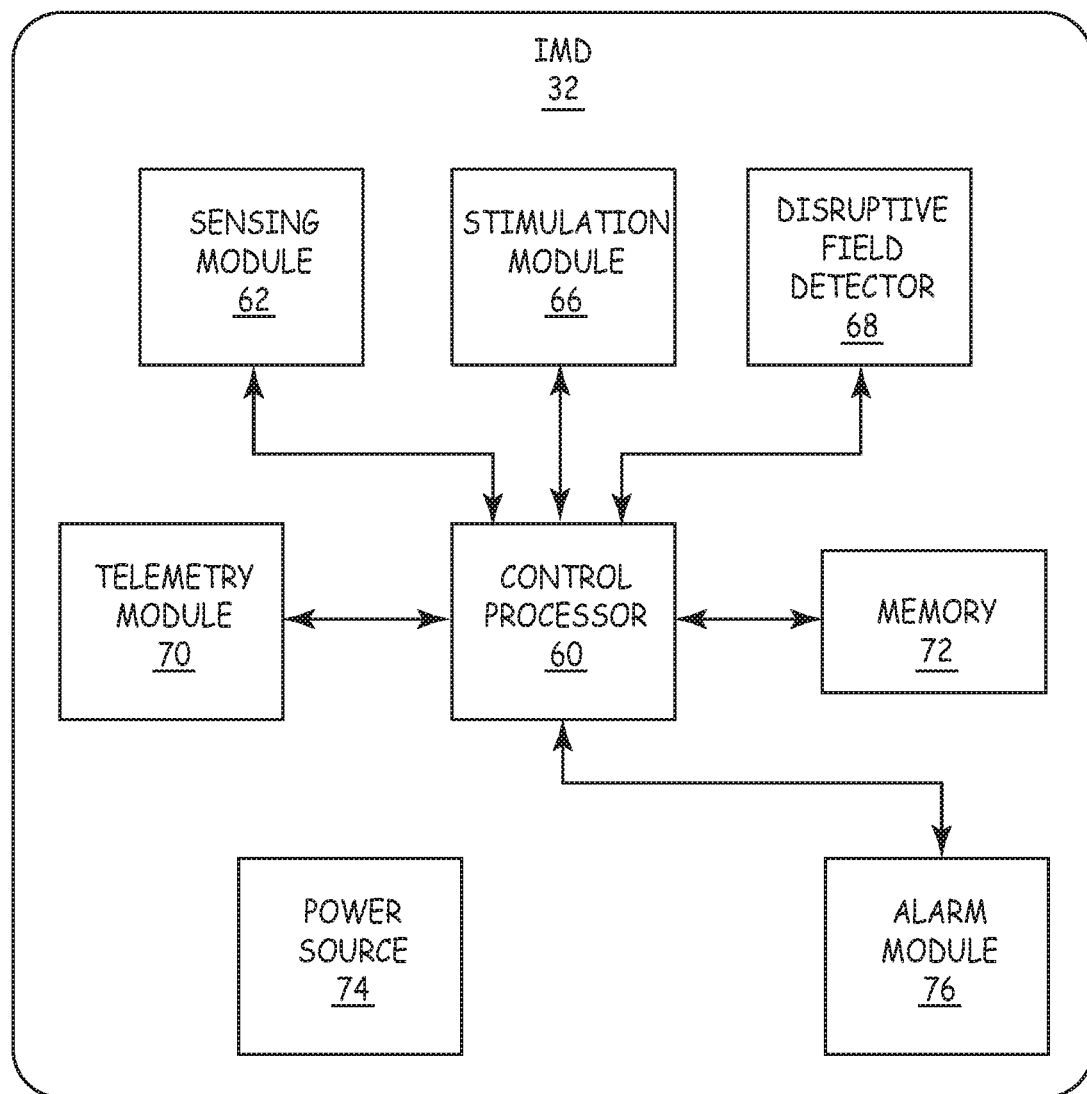
FIG. 4 is a functional block diagram of an example configuration of components of the IMD of FIG. 3.

FIG. 4 is a functional block diagram of an example configuration of components of IMD 32. In the example illustrated by FIG. 4, IMD 32 includes a control processor 60, sensing module 62, stimulation module 66, disruptive field detector 68, telemetry module 70, memory 72, power source 74 and alarm module 76. Memory 72 may include computer-readable instructions that, when executed by control processor 60 or other component of IMD 32, cause one or more components of IMD 32 to perform various functions attributed to those components in this disclosure. Memory 72 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other storage media.

The various components of IMD 32 are coupled to power source 74, which may include a rechargeable or non-rechargeable battery. A non-rechargeable battery may be capable of holding a charge for several years, while a rechargeable battery may be inductively charged from an external device, e.g., on a daily or weekly basis. Power source 74 also may include power supply circuitry for providing regulated voltages and/or current levels to power the various components of IMD 32.

Control processor 60 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. The functions attributed to control processor 60 herein may be embodied as software, firmware, hardware or any combination thereof.

Under the control of processor 60, telemetry module 70 may receive downlink telemetry from and send uplink telemetry to programming device 18 or access point 20 with the aid of an antenna, which may be internal and/or external to IMD 32. Telemetry module 70 includes any suitable hardware, firmware, software or any combination thereof for communicating with another device, such as programming device 18. For example, telemetry module 70 may include appropriate modulation, demodulation, encoding, decoding, frequency conversion, filtering, and amplifier components for transmission and reception of data.

Control processor 60 controls stimulation module 66 to deliver electrical stimulation therapy to heart 38 via one or more of electrodes 44, 46, 50, 52 and/or the housing electrode (FIG. 3). Stimulation module 66 is electrically coupled to electrodes 44, 46, 50 and 52, e.g., via conductors of the respective lead 34 and 36, or, in the case of the housing electrode, via an electrical conductor disposed within the housing of IMD 32. Control processor 60 controls stimulation module 66 to deliver electrical pacing pulses with the amplitudes, pulse widths, rates, electrode combinations or electrode polarities specified by a selected therapy program. For example, electrical stimulation module 66 may deliver bipolar pacing pulses via ring electrodes 46 and 52 and respective corresponding helical tip electrodes 44 and 50 of leads 34 and 36, respectively. Stimulation module 66 may deliver one or more of these types of stimulation in the form of other signals besides pulses or shocks, such as sine waves, square waves, or other substantially continuous signals. In addition to pacing pulses, stimulation module 66 may, in some instances, deliver other types of electrical therapy, such as defibrillation therapy or cardioversion therapy.

Stimulation module 66 may include a switch module (not shown) and control processor 60 may use the switch module to select, e.g., via a data/address bus, which of the available electrodes are used to deliver pacing, resynchronization, cardioversion, or defibrillation therapy. The switch module may include a switch array, switch matrix, multiplexer, or any other type of switching device suitable to selectively couple stimulation energy to selected electrodes.

Sensing module 62 is configured to receive signals from one or more sensors. In one example, sensing module 62 is configured to receive signals sensed by one or more of electrodes 44, 46, 50, 52 and the housing electrode. In this manner, electrodes 44, 46, 50, 52, and the housing electrode may operate as sense electrodes in addition to or instead of being used for delivering electrical stimulation therapy. In other instances, leads 34 and 36 may include one or more electrodes dedicated for sensing. In further examples, sensing module 62 is coupled to one or more sensors that are not included on leads 34 and 36, e.g., via a wired or wireless coupling. Such sensors may include, but are not limited to, pressure sensors, accelerometers, flow sensors, blood chemistry sensors, activity sensors or other type of physiological sensor. Signals monitored by sensing module 62 may be stored in memory 72.

Sensing module 62 may receive signals sensed by any number of sensing configuration defined by various combinations of one or more of electrodes 44, 46, 50 and 52. Control processor 60 may select the electrodes that function as sense electrodes, sometimes referred to as a sensing configuration or sensing vector, in order to monitor electrical activity of heart 30. In one example, sensing module 62 may include a switch module (not shown) to select which of the available electrodes are used to sense the heart activity. Control processor 60 may select the electrodes that function as sense electrodes, or the sensing electrode configuration, via the switch module within sensing module 62, e.g., by providing signals via a data/address bus.

Sensing module 62 may store the sensed signals in memory 72. In some instances, sensing module 62 may store the sensed signals in raw form. In other instances, sensing module 62 may process the sensed signals and store the processed signals in memory 72. Sensing module 62 may, for example, include multiple detection channels configured to detect different cardiac events, such as intrinsic or paced atrial events, intrinsic or paced ventricular events, repolarization of the ventricles, and the like. Each of the detection channels may comprise an amplifier, filter or other components. Sensing module 62 may amplify and filter the sensed signal and store the filtered signal in memory 72. The signals stored by sensing module 62 may, in some cases, be retrieved and further processed by control unit 60.

As described above, processor 60 may be configurable to operate IMD 32 in a number of different operating modes, such as the normal operating mode and the exposure operating mode. Although the techniques of this disclosure are described with respect to two operating modes, i.e., the normal and exposure mode, processor 60 may operate IMD 32 in accordance with and switch between more than two operating modes. In the normal operating mode, processor 60 operates IMD 32 in accordance with settings programmed by a physician, clinician or other user. The normal operating mode may correspond with the operating mode that a physician or other user feels provides a most efficacious therapy for patient 12. The normal operating mode may vary from patient to patient depending on the condition of patient 12 for which IMD 32 is providing therapy.

The normal operating mode of IMD 32 may be one or more of any of a number of pacing modes, including DDD, VVI, DVI, VDD, AAI, DDI, DDDR, VVIR, DVIR, VDDR, AAIR, DDIR, VOO, AOO, DOO, ODO and other modes of single and dual-chamber pacing or sensing. For example, the normal operating mode may be an atrial based pacing mode, such as AAI or ADI pacing mode, if IMD 32 is providing therapy to a patient experiencing bradycardia. As another example, the normal operating mode may be a dual-chamber pacing mode, such as a DDD pacing mode, if IMD 32 is providing therapy to a patient with unreliable A-V conduction.

In the aforementioned operating modes, the abbreviations of which conform to the NBG Pacemaker Code, the first letter in the pacing mode indicates the chamber or chambers paced and may take on the letter "D" indicating dual-chamber (i.e., atrial and ventricle both paced), "V" indicating a ventricle is paced, "A" indicating an atrium is paced, or "O" indicating no chamber is paced. The second letter indicates the chamber or chambers sensed and may take on the letter "D" indicating dual-chamber (i.e., atrial and ventricle both paced), "V" indicating a ventricle is paced, "A" indicating an atrium is paced, or "O" indicating no chamber is paced. The third letter indicates mode or modes of response to sensing and may take on the letter "T" indicating triggered pacing (i.e., pacing is provided in response to the sensing), "I" indicating inhibited pacing (i.e., pacing is stopped based in response to the sensing), "D" indicating dual response (i.e., triggered and inhibited) and "O" for no response. The fourth letter indicates programmable functions and may take on the letter "R" indicating rate modulated pacing, as well as other letters not explained here. Although not described here, a fifth letter may be provided in accordance with the NBG Pacemaker Code indicating anti-tachycardia functions.

When IMD 32 is configured to generate and deliver pacing pulses to heart 30, control processor 60 controls a pacer timing and control module (not shown), which may be embodied as hardware, firmware, software, or any combination thereof. The pacer timing and control module may comprise a dedicated hardware circuit, such as an ASIC, separate from other components of control processor 60, such as a microprocessor, or comprise a software module executed by a component of control processor 60, which may be a microprocessor or ASIC.

The pacer timing and control module may include programmable counters which control the basic time intervals associated with various single and dual-chamber pacing modes. Intervals defined by the pacer timing and control module within control processor 60 may include, for example, atrial and ventricular pacing escape intervals and refractory periods during which sensed atrial and ventricular events are ineffective to restart timing of the escape intervals. As another example, the pace timing and control module may define a blanking period, and provide signals to sensing module 62 to blank one or more channels, e.g., amplifiers, for a period during and after delivery of electrical stimulation to heart 30. The durations of these intervals may be determined by control processor 60 in response to stored program data in memory 72. The pacer timing and control module of control processor 60 may also determine the amplitude and pulse width of the cardiac pacing pulses.

During pacing, escape interval counters within the pacer timing and control module of control processor 60 may be reset upon sensing of R-waves and P-waves with detection channels of sensing module 62. Additionally, the value of the count present in the escape interval counters when reset by sensed R-waves and P-waves may be used by control processor 60 to measure the durations of R-R intervals, P-P intervals, P-R intervals and R-P intervals, which are measurements that may be stored in memory 72. Control processor 60 may analyze these various intervals to determine conditions of heart 30, such as to detect a tachyarrhythmia event. When IMD 32 is capable of providing defibrillation therapy, the R-R intervals may be used to increment a VF counter to control delivery of cardioversion or defibrillation shocks. For example, the VF counter may be incremented in response to detection of short R-R intervals, and possibly in response to other events such as R-R interval variance. The VF counter triggers delivery of a defibrillation shock when the counter reaches a number of intervals for detection (NID) threshold. Additionally, control processor 60 may begin an anti-tachyarrhythmia pacing regimen prior to delivery of the defibrillation shock.

The normal operating mode may be susceptible to undesirable operation when IMD 32 is placed within environment 10 with disruptive energy field 11. In some instances, sensing module 62 inappropriately detects the induced energy on the leads as physiological signals (e.g., intrinsic cardiac events). In other words, IMD 32 senses a physiological signal when one is not actually present. At the very least, the detection of the induced energy caused by disruptive energy field 11 results in the stored data not accurately representing the actual function and condition of heart 38. Moreover, the detection of the induced energy caused by disruptive energy field 11 may in turn cause undesirable operation of IMD 32.

For example, when the current or normal operating mode is a pacing mode with inhibit response to sensing, processor 60 may not deliver (i.e., withhold) a desired pacing pulse in response to sensing the induced energy from disruptive energy field 11 as a physiological signal. For example, processor 60 may identify the induced energy as a ventricular event. This may result in control processor 60 resetting the ventricular escape interval counter, thereby inhibiting delivery of a desired pacing pulse. In other instances when the normal operating mode is a dual chamber pacing mode with inhibit and trigger response to sensing, processor 60 may also deliver an undesirable pacing pulse in addition to withholding a desired pacing pulse in response to sensing the induced energy from disruptive energy field 11 as a physiological signal. In particular, sensing the induced energy from the disruptive energy field as a physiological signal may inappropriately start an escape interval after which an undesired pacing pulse is delivered. This may result in dangerously fast heart rhythms and may lead to tachyarrhythmia or fibrillation.

In other instances, the induced energy on the leads may result in IMD 32 not sensing actual physiological signals that are present. Processor 60 may, for example, initiate a blanking period in response to the induced energy on the leads. During the blanking period, sensing module 62 may power down one or more sense amplifiers. As such, sensing module 62 will fail to detect any intrinsic physiological event that occurs during the blanking period. Failure to detect this actual physiological event may again result in IMD 32 delivering undesired therapy or withholding desired therapy.

In further instances, the induced energy on one or more of leads 34 and 36 may result in inadvertent stimulation or heating of the tissue and/or nerve site adjacent to any of electrodes 44, 46, 50 and 52 of respective leads 34 and 36. Such heating may result in thermal damage to the tissue adjacent the electrodes. This may in turn possibly compromise pacing and sensing thresholds at the site.

To reduce the adverse effects of disruptive energy field 11, control processor 60 may be configured to operate IMD 32 in the exposure operating mode. The exposure operating mode is typically less susceptible to undesirable operation in disruptive energy field 11 than the normal operating mode. In other words, operating IMD 32 in the exposure mode may reduce if not eliminate some or all of the adverse effects that disruptive energy field 11 have on therapy delivery to patient 12. When operating in the exposure operating mode, control processor 60 is configured to operate with different functionality compared to the normal operating mode. Processor 60 may, in some instances, be configured to operate with reduced functionality. For example, processor 60 may not provide sensing, not deliver therapy, delivery only a subset of possible therapies, not log collected data or the like. In other instances, processor 60 may be operating with approximately the same functionality or even increased functionality in the exposure mode. For example, processor 60 may use a different sensor or algorithm to detect cardiac activity of the heart of patient 12, such as pressure sensor measurements rather than electrical activity of the heart.

Processor 60 automatically determines at least a portion of the parameters and, in some instances all of the parameters, of the exposure operating mode based on stored information regarding sensed physiological events and/or therapy provided over a predetermined period of time. To that end, processor 60 may include an exposure mode parameter determination module that analyzes the stored information to generate the one or more parameters. In automatically determining the parameters of the exposure operating mode, processor 60 is particularly interested in stored information pertaining to physiological events and therapy within a short period of time prior to the determination. Processor 60 may analyze the data regarding sensed physiological events and/or therapy provided within the last hour, two hours, four hours, or other predetermined period of time which may be configured by the physician. To the contrary, processor 60 may analyze stored information over a much longer period of time, e.g., a day, week or even longer, during normal device operation to identify trends, diagnose the efficacy of the therapy, or the like.

Processor 60 may periodically determine the parameters of the exposure operating mode. For example, processor 60 may periodically determine the parameters of the exposure operating mode every hour, two hours, four hours, daily, or the like. In some instances, processor 60 may continuously determine the parameters of the exposure operating mode on the periodic basis. In other instances, IMD 32 may begin to periodically determine the parameters of the exposure operating mode in response to some event, e.g., in response to receiving a command from a programmer, a home monitoring system, a hand-held patient monitor or the like, either directly or remotely via network 22. For example, a physician may send a command to IMD 32 to notify IMD 32 that an MRI scan will be performed and, in response to the command, processor 60 may automatically determine the parameters of the exposure operating mode. As another example, processor 60 may begin to periodically determine the parameters of the exposure operating mode after a physician manually programs an initial set of exposure operating mode parameters. In this manner, IMD 32 may notify the physician and/or automatically change the exposure operating mode parameters if the automatically generated parameters differ from the manually programmed parameters. In some cases, IMD 32 may require that the automatically generated parameters differ significantly from the manually programmed parameters before notifying the physician of the differences and/or automatically changing the exposure operating mode parameters. As described in further detail below, whether a difference is determined to be significant may be determined differently depending on the circumstances of a particular patient 12, the physician treating the patient or the like.

As a further example, processor 60 may automatically determine the parameters of the exposure operating mode in response to detecting exposure to environment 10. Processor 60 may, for instance, automatically determine the parameters of the exposure operating mode in response to detecting a static magnetic field having an amplitude corresponding with MRI scanner 16, and configure IMD 32 to operate in accordance with the parameters prior to exposure to the gradient or RF fields of MRI scanner 16. In this case, disruptive energy field detector 68 may be a Hall sensor or other magnetic field sensor.

In automatically determining the parameters of the exposure operating mode, processor 60 may analyze any of a variety of information stored in memory 72 related to sensed physiological events and/or therapy provided. For example, processor 60 may determine whether any therapy was provided over the predetermined period of time and, if any therapy was provided, the parameters of the therapy provided. The parameters of the therapy provided that may be analyzed by processor 60 include operating modes in which the device operated, percentage of time during which therapy is provided, amplitudes of the therapy energy delivered, pulse widths of the therapy energy delivered, PAV intervals (i.e., the amount of time that elapsed between a paced atrial event a paced ventricular event), pacing capture thresholds (e.g., rheobase and chronaxie), sensing amplitudes, arrhythmias or the like. Additionally, processor 60 may analyze sensed information or information determined based on sensed information to automatically determine the parameters of the exposure operating mode. For example, IMD 32 may analyze the heart rate of patient 12 during the predetermined period of time.

Based on the analysis of the stored information, processor 60 determines one or more parameters of the exposure operating mode. Processor 60 may determine an operating mode to use when programmed into the exposure operating mode based on a pacing percentage and/or a previous pacing mode. For example, processor 60 may determine a pacing percentage for the predetermined period of time (e.g., 1-4 hours). The pacing percentage may be computed by dividing the number of cardiac cycles during which a pacing pulse was delivered during the predetermined period of time by the total number of cardiac cycles during the predetermined period of time. If the pacing percentage is less than a threshold pacing percentage (e.g., 5%), processor 60 selects a sense-only operating mode as the exposure operating mode, e.g., ODO, OAO, or OVO. Because there is no pacing in these operating modes, such operating modes may prevent processor 60 from delivering undesirable stimulation or withholding desirable stimulation.

If the pacing percentage is greater than or equal to the threshold pacing percentage, processor 60 selects an operating mode in which pacing therapy is provided. In other words, if the pacing percentage is greater than or equal to the threshold pacing percentage, processor 60 may operate as if patient 12 is pacing dependent and select an operating mode in which asynchronous pacing is provided. The asynchronous pacing mode may have no sensing functionality, e.g., AOO, VOO or DOO pacing mode, or include sensing functionality but have no mode of response to the sensing, e.g., AAO, AVO, ADO, VVO, VAO, VDO, DDO, DAO or DVO pacing mode. In either of these cases, the pacing provided is not responsive to the sensing, e.g., no trigger or inhibit functionality. As such, the induced energy on the leads caused by disruptive energy field 11 does not result in undesirable operation of IMD 32. The threshold pacing percentage may be programmed by a physician and may take on a higher or lower value. In one instance the threshold percentage may be 0% such that if any pacing is delivered within the predetermined period of time, an operating mode in which pacing therapy is delivered is selected.

When processor 60 determines that the exposure operating mode should be a pacing mode, e.g., the pacing percentage is greater than or equal to the threshold pacing percentage, processor 60 may analyze the previous operating modes to determine which of the pacing modes to select. Processor 60 may, for example, select the dual-chamber pacing mode (e.g., DOO) if IMD 32 has been operated in any dual-chamber mode during the predetermined time period. If IMD 32 has not been operated in any dual-chamber mode during the predetermined time period, processor 60 selects either a ventricular-based pacing mode (e.g., VOO) or an atrial based pacing mode (e.g., AOO) based on the previously configured mode. As described above, however, processor 60 may select a pacing mode that includes sensing functionality but the pacing is not responsive to the sensing, e.g., no trigger or inhibit functionality.

Additionally, processor 60 may determine one or more parameters of the pacing modes based on the stored information, such as a pacing rate, a pacing amplitude, a pacing width, a PAV interval or the like. Processor 60 may analyze an average heart rate during the predetermined period of time and select a pacing rate for the pacing pulses delivered exposure operating mode based on the analysis. For example, processor 60 may set a pacing rate of 85 beats per minute (bpm) for the selected pacing mode when the average heart rate during the predetermined period of time is less than or equal to a threshold heart rate (e.g., 65 bpm) and set the pacing rate to 25 percent higher than the average heart rate when the average heart rate during the predetermined period of time is greater than the threshold heart rate.

Alternatively, or additionally, processor 60 may analyze pacing amplitudes during the predetermined period of time and select a pacing amplitude for the pacing pulses delivered during the exposure operating mode based on the analysis. For example, processor 60 may set the pacing amplitude for pacing pulses delivered during the exposure operating mode at a predetermined voltage (e.g., 5 Volts (V)) when the highest pacing amplitude of the predetermined period of time is less than a threshold pacing amplitude (e.g., 5 V) and set the pacing amplitude for pacing pulses delivered during the exposure operating mode equal to the highest pacing amplitude of the predetermined period of time when the highest pacing amplitude of the predetermined period of time is greater than or equal to the threshold pacing amplitude. The predetermined voltage and the threshold pacing amplitude do not need to be the same value.

Alternatively, or additionally, processor 60 may analyze pacing pulse widths during the predetermined period of time and select a pacing pulse width for the pacing pulses delivered during the exposure operating mode based on the analysis. For example, processor 60 may set the pacing pulse width for pacing pulses delivered during the exposure operating mode to a predetermined width (e.g., 1 millisecond (ms)) when the highest pacing pulse width during the predetermined period of time is less than a threshold pulse width (e.g., 1 ms) and set the pacing pulse width for pacing pulses delivered during the exposure operating mode equal to the highest pacing pulse width of the predetermined period of time when the highest pacing pulse width of the predetermined period of time is greater than or equal to the threshold pulse width. The predetermined pulse width and the threshold pulse width do not need to be the same value.

When processor 60 selects a dual-chamber pacing mode for the exposure operating mode, processor 60 may analyze PAV intervals during the predetermined period of time and select a PAV interval for the exposure operating mode based on the analysis. For example, processor 60 may set the PAV interval for the exposure operating mode to a first predetermined interval (e.g., 110 ms) when the average PAV interval during the predetermined period of time is greater than or equal to a first threshold PAV interval (e.g., 110 ms), set the PAV interval to the average PAV interval when the average PAV interval is less than the first PAV interval threshold and greater than or equal to a second PAV interval threshold (e.g., 50 ms), and set the PAV interval to a second predetermined interval (e.g., 50 ms) when the average PAV interval is less than the second threshold PAV interval. The threshold PAV intervals and the predetermined PAV intervals do not need to be the same values.

Processor 60 may also suspend some functionality, e.g., diagnostic and counters, magnet mode, tachyarrhythmia and PVC detection, tachyarrhythmia therapies, or the like. A summary of an example automatic determination criteria and the resulting selected parameters of the exposure operating mode is provided in Table 1 below. Table 1 is for example purposes only and should not be considered limiting of the techniques as broadly described in this disclosure. The various thresholds and corresponding setting may be adjusted based on various considerations.

TABLE 1

| System Parameters | Conditions | Exposure Mode Settings |
| --- | --- | --- |
| Pacing Mode | Pacing percentage <5% | ODO |
| | 1) Pacing percentage ≥5% | |
| | 2) Previous dual-chamber mode | DOO |
| | 1) Pacing percentage ≥5% | |
| | 2) Previous ventricular chamber mode | VOO |
| | 1) Pacing percentage ≥5% | |
| | 2) Previous atrial chamber mode | AOO |
| Pacing Rate | Avg Heart Rate ≤65 bpm | 85 bpm |
| | Avg Heart Rate >65 bpm | 1.25 * Avg Heart Rate |
| Pacing Amplitude | Max Pacing Amplitude <5 V | 5 V |
| | Max Pacing Amplitude ≥5 V | Max Pacing Amplitude |
| Pacing Pulse Width | Max Pacing Pulse Width <1 ms | 1 ms |
| | Max Pacing Pulse Width ≥1 ms | Max Pacing Pulse Width |
| PAV interval | 1) Pacing mode = DOO | |
| | 2) Avg PAV interval ≥110 ms | 110 ms |
| | 1) Pacing mode = DOO | |
| | 2) 110 ms > Avg PAV interval ≥50 ms | Avg PAV interval |
| | 1) Pacing mode = DOO | |
| | 2) Avg PAV interval <50 ms | 50 ms |

Table 1 provides an example of the type of stored information that may be used in selecting parameters of the exposure operating mode. Processor 60 may analyze other stored information in addition to or instead of the system parameters described above. For example, processor 60 may analyze pacing capture thresholds measured during the predetermined period of time and select an amplitude and/or pulse width for pacing pulses to be delivered during the exposure operating mode based on the analysis. As another example, processor 60 may analyze measured sensing amplitudes during the predetermined period of time and select one of a sensing threshold and/or pacing mode to used during the exposure operating mode based on the analysis. As a further example, processor 60 may analyze the arrhythmia episodes during the predetermined period of time and select a pacing mode to be used during the exposure operating mode based on the analysis.

Processor 60 stores the automatically determined parameters of the exposure operating mode and uses at least a portion of the parameters when it is configured to operate in the exposure operating mode. Processor 60 may be configured to operate IMD 32 in the exposure mode at some time prior to being exposed or immediately upon being exposed to disruptive energy field 11. In one instance, processor 60 may configure IMD 32 to operate in accordance with the automatically determined parameters in response to detecting disruptive energy field 11. In this case, IMD 32 may be a fully automated MR Conditional or MR Safe device that does not require any manual programming of the exposure operating mode parameters.

To this end, processor 60 may include one or more sensors, such as a disruptive field detector 68, that detect the presence of disruptive energy field 11. Disruptive field detector 68 may include a magnetic field detector, such as a Hall sensor or a reed switch. In some instances, disruptive field detector 68 may be within housing 70 of IMD 32. For example, disruptive field detector 68 may be the same field detector used to sense a magnetic programming head of a programming device. Alternatively, IMD 32 may be coupled to a disruptive field detector 68 located outside of housing 70 of IMD 32.

Control processor 60 may receive one or more signals from disruptive field detector 68. The signal produced by disruptive field detector 68 may, for example, identify that patient 12 has entered an environment in which IMD 32 is exposed to an energy field, e.g., a magnetic field, that is greater than or equal to a threshold level indicative of a disruptive energy field 11. In one example, processor 60 may utilize all or a subset of the detection methods described in U.S. Pat. No. 6,937,726 to Terry et al., entitled, "METHOD AND APPARATUS FOR DETECTING STATIC MAGNETIC FIELDS," which issued on Aug. 30, 2005 and which is incorporated herein by reference in its entirety. However, other disruptive field detection methodologies may also be employed by processor 60 in other examples to detect the presence of disruptive energy field 11, which may in one example be the static magnetic field of MRI scanner 16, the gradient magnetic fields of MRI scanner 16, or the RF fields of MRI scanner 16.

In another example, processor 60 may receive, e.g., via telemetry, parameters for the exposure operating mode from a physician, clinician, or other person. In some instances, processor 60 may have already automatically determined suggested parameters for the exposure operating mode. In this case, processor 60 may compare the previously determined parameters with the parameters that were received and alert the physician if there are any differences and, in some instances, significant differences, between the two sets of parameters. In other instances, the manually entered parameters may not be different from the automatically determined parameters at the time the parameters are manually received from the physician, but may differ at a later period of time, e.g., due to do a changing condition of a patient. If there are discrepancies between the automatically determined parameters and the manually programmed parameters, IMD 32 may initiate an alert to patient 12 and/or physician notifying them that the automatically determined parameters differ from the manually programmed parameters. For example, processor 60 may cause telemetry module 70 to transmit an alert or other signal, e.g., via access point 20, network 22 and one of computing devices 26, to notify a physician, clinician or technician of discrepancy. In this manner, the telemetry signal may function as the alert mechanism. IMD 32 may generate an alert perceptible to patient 12 in addition to or instead of the alert to the physician. Alarm module 76 may include alarm circuitry to provide an audible alert, a perceptible muscle vibration, muscle stimulation or other sensory stimulation to notify the patient that an alert condition has been detected, e.g., a discrepancy between the manually programmed and automatically determined parameters.

Alternatively or additionally, IMD 32 may provide the automatically determined parameters to the physician or clinician at the time of the manual programming. In other words, IMD 32 may recommend appropriate parameters for the exposure operating mode. Processor 60 may transmit the automatically determined parameters to a programming device 18 (or remote computing device 26) for display to the physician or clinician. The physician, clinician or other user may review the recommended parameters and accept the suggested parameters or adjust one or more of the suggested parameters.

In any case, IMD 32 may continue to automatically determine the parameters to ensure that a change in condition of patient 12 does not change the recommended parameters of the exposure operating mode. For example, suppose a physician manually configures the parameters of the exposure operating mode to be a sensing-only mode (e.g., ODO). After the manual configuration of the exposure operating mode, patient 12 is paced during the normal operating mode such that the pacing percentage exceeds the threshold pacing percentage. IMD 32 automatically determines, prior to the MRI scan, that the recommended parameters of the exposure operating mode are a pacing mode instead of sense-only mode due to the fact that the pacing percentage threshold is exceeded. IMD 32 may notify the physician of such a discrepancy. Alternatively, or additionally, IMD 32 may notify the patient to revisit the physician prior to the scan. In yet another embodiment, IMD 32 may simply override the manually programmed parameters with the automatically configured parameters, e.g., override the sensing-only mode by the appropriate pacing mode. As such, automatically determining the parameters of the exposure operating mode provides an added safety mechanism in case the condition of the patient changes from the time between the manual programming of the parameters of the exposure operating mode and the MRI scan. Similar alerts or overriding changes may occur with respect to other exposure operating mode parameters, such as pacing pulse amplitude, pacing pulse width, pacing rate, PAV interval or the like. In this manner, IMD 32 may continue to update the parameters of the exposure operating mode until just before exposure to disruptive energy field 11.

In some instances, processor 60 may determine whether to override the parameters or notify the patient and/or physician based on the differences. For example, processor 60 may override the parameters in instances in which the difference does not represent a major difference, e.g., a slight change in pulse amplitude, pulse width or pacing rate. However, processor 60 may not override the differing parameters when the change may be viewed as major, e.g., changing from a pacing-only mode to a sense-only mode or the like.

IMD 32 may revert back to the normal operating mode after exiting environment 10. For example, IMD 32 may be manually configured from the exposure operating mode to the normal operating mode using programming device 18 or remotely via network 22. As another example, IMD 32 may automatically configure itself from the exposure operating mode to the normal operating mode after determining that IMD 32 has exited environment 10, e.g., in response to disruptive energy field detector 68 no longer detecting disruptive energy field 11. As a further example, IMD 32 may automatically configure itself from the exposure operating mode to the normal operating mode after a predetermined period of time expires. In response to detecting a disruptive energy field, it is desirable that processor 60 be reconfigured from the exposure operating mode to the normal operating mode as soon as safely possible after exiting from environment 10, e.g., due to the reduced or otherwise different functionality of the exposure mode. The techniques of this disclosure may be used to automatically revert processor 60 back to the normal operating mode when particular criteria that are indicative of the MRI being complete occur.

Figure 5:
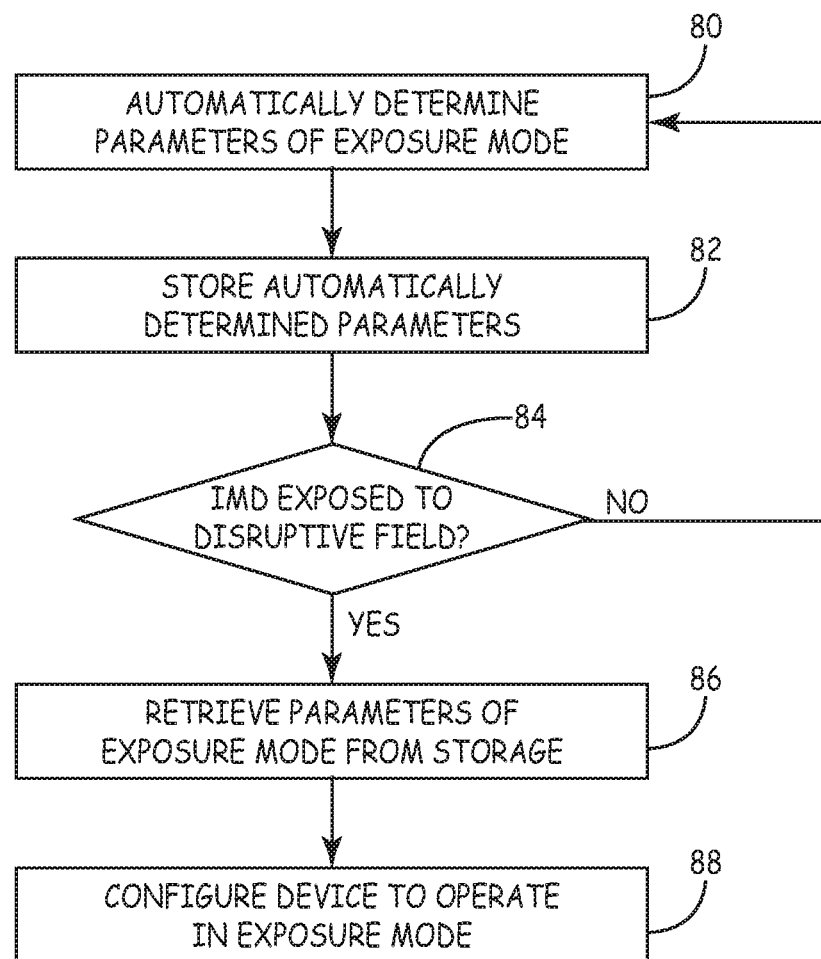
FIG. 5 is a flow diagram illustrating example operation of an IMD in accordance with one aspect of this disclosure.

FIG. 5 is a flow diagram illustrating example operation of an IMD, such as IMD 14 or 32, in accordance with one aspect of this disclosure. Initially, processor 60 automatically determines at least a portion of the parameters and, in some instances all of the parameters, of the exposure operating mode (80). As described above, processor 60 may periodically determine the parameters of the exposure operating mode, e.g., every hour, two hours, four hours or the like. In automatically determining the parameters of the exposure operating mode, processor 60 may analyze any of a variety of stored information related to sensed physiological events and/or therapy provided over a predetermined period of time, including, but not limited to pacing modes in which the device operated, percentage of time during which therapy is provided, amplitudes of the therapy energy delivered, pulse widths of the therapy energy delivered, rate at which the therapy energy was delivered, average heart rate, peak heart rate, PAV intervals, pacing capture thresholds (e.g., rheobase and chronaxie), sensing amplitudes, arrhythmias or the like. Processor 60 stores the automatically determined parameters in memory 72 or other storage mechanism (82).

Processor 60 determines whether IMD 32 is exposed to disruptive energy field 11 (84). Control processor 60 may, for example, receive one or more signals from disruptive field detector 68 indicating that patient 12 has entered an environment in which IMD 32 is exposed to disruptive energy field 11, which may in one example be the static magnetic field of MRI scanner 16, the gradient magnetic fields of MRI scanner 16, or the RF fields of MRI scanner 16. When processor 60 determines that IMD 32 is not exposed to disruptive energy field 11 ("NO" branch of 84), processor 60 continues to automatically determine parameters of the exposure operating mode.

When processor 60 determines that IMD 32 is exposed to the disruptive energy field 11 ("YES" branch of 84), e.g., in response to receiving a signal from disruptive energy field detector 68, processor 60 retrieves the automatically determined parameters of the exposure operating mode from memory 72 (86) and configures IMD 32 in accordance with the retrieved parameters (88). In this case, IMD 32 may be a fully automated MR Conditional or MR Safe device that does not require any manual programming of the exposure operating mode parameters.

Figure 6:
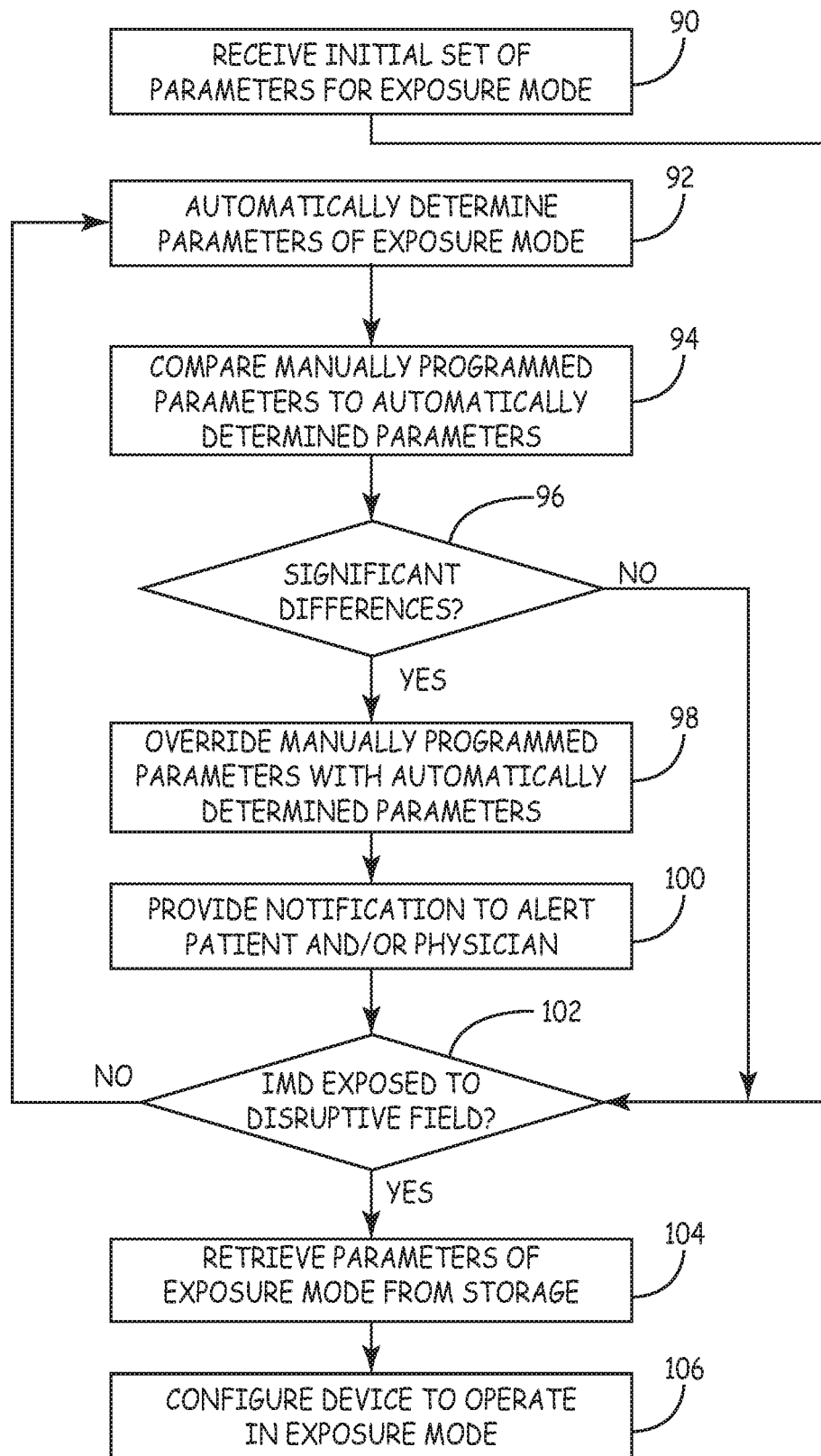
FIG. 6 is a flow diagram illustrating example operation of an IMD in accordance with another aspect of this disclosure.

FIG. 6 is a flow diagram illustrating example operation of an IMD, such as IMD 14 or 32, in accordance with another aspect of this disclosure. Processor 60 receives, e.g., via telemetry, parameters for the exposure operating mode from a physician, clinician, or other user of an external device (90). In other words, the user of the external device manually programs the parameters of the exposure operating mode.

Processor 60 determines whether IMD 32 is exposed to disruptive energy field 11 (102). Control processor 60 may, for example, receive one or more signals from disruptive field detector 68 indicating that patient 12 has entered an environment in which IMD 32 is exposed to disruptive energy field 11, which may in one example be the static magnetic field of MRI scanner 16, the gradient magnetic fields of MRI scanner 16, or the RF fields of MRI scanner 16. When processor 60 determines that IMD 32 is exposed to the disruptive energy field 11 ("YES" branch of 102), e.g., in response to receiving a signal from disruptive energy field detector 68, processor 60 retrieves the parameters of the exposure operating mode from memory 72 (104) and configures IMD 32 in accordance with the retrieved parameters (106).

When processor 60 determines that IMD 32 is not exposed to disruptive energy field 11 ("NO" branch of 102), processor 60 automatically determines parameters of the exposure operating mode using stored information regarding sensed physiological events and/or delivered therapies (92). In one instance, processor 60 may automatically determine the parameters of the exposure operating mode prior to receiving the manually programmed parameters from the external device. In this case, processor 60 may recommend a set of parameters for the exposure operating mode to the user via the external device to assist the user in determining the parameters to manually program. The physician, clinician or other user may review the recommended parameters and accept the suggested parameters or adjust one or more of the suggested parameters. In other instances, processor 60 may begin to automatically determine the parameters of the exposure operating mode after receiving the manually programmed parameters.

Processor 60 compares the manually programmed parameters received from the user to the automatically determined parameters (94). The differences between the parameters may be differences in operating modes (e.g., sensing-only mode vs. pacing mode), differences in pacing parameters (e.g., pacing pulse amplitude, pacing pulse width, pacing rate, PAV interval) or other differences.

If there are no significant differences ("NO" branch of 96), processor 60 continues to determine whether the IMD is exposed to disruptive energy field 11. If there are significant differences between the automatically determined parameters and the manually programmed parameters ("YES" branch of 96), processor 60 may override the manually programmed parameters with the automatically determined parameters (98). IMD 32 may also provide a notification to alert patient 12 and/or physician that the most recent automatically determined parameters differ from the manually programmed parameters (100). For example, processor 60 may cause telemetry module 70 to transmit an alert or other signal to programming device 18 or one of the computing devices 26 to notify the physician of discrepancy, or generate an alert perceptible to patient 12 in addition to or instead of the alert to the physician. In response to the alert, patient 12 may revisit the physician or the physician may remotely approve replacing the manually programmed parameters with the automatically generated parameters. Although described as performing the automatic override and patient/physician alert, processor 60 may only override, only alert or perform some other completely different action. Additionally, the actions are described as being performed when there are "significant" differences. However, similar techniques may be used for any differences, whether significant or non-significant.

In this manner, IMD 32 may continue to update the parameters of the exposure operating mode until just before exposure to disruptive energy field 11 thereby providing an added safety mechanism in case the condition of the patient changes from the time between the manual programming of the parameters of the exposure operating mode and the MRI scan.

Figure 7:
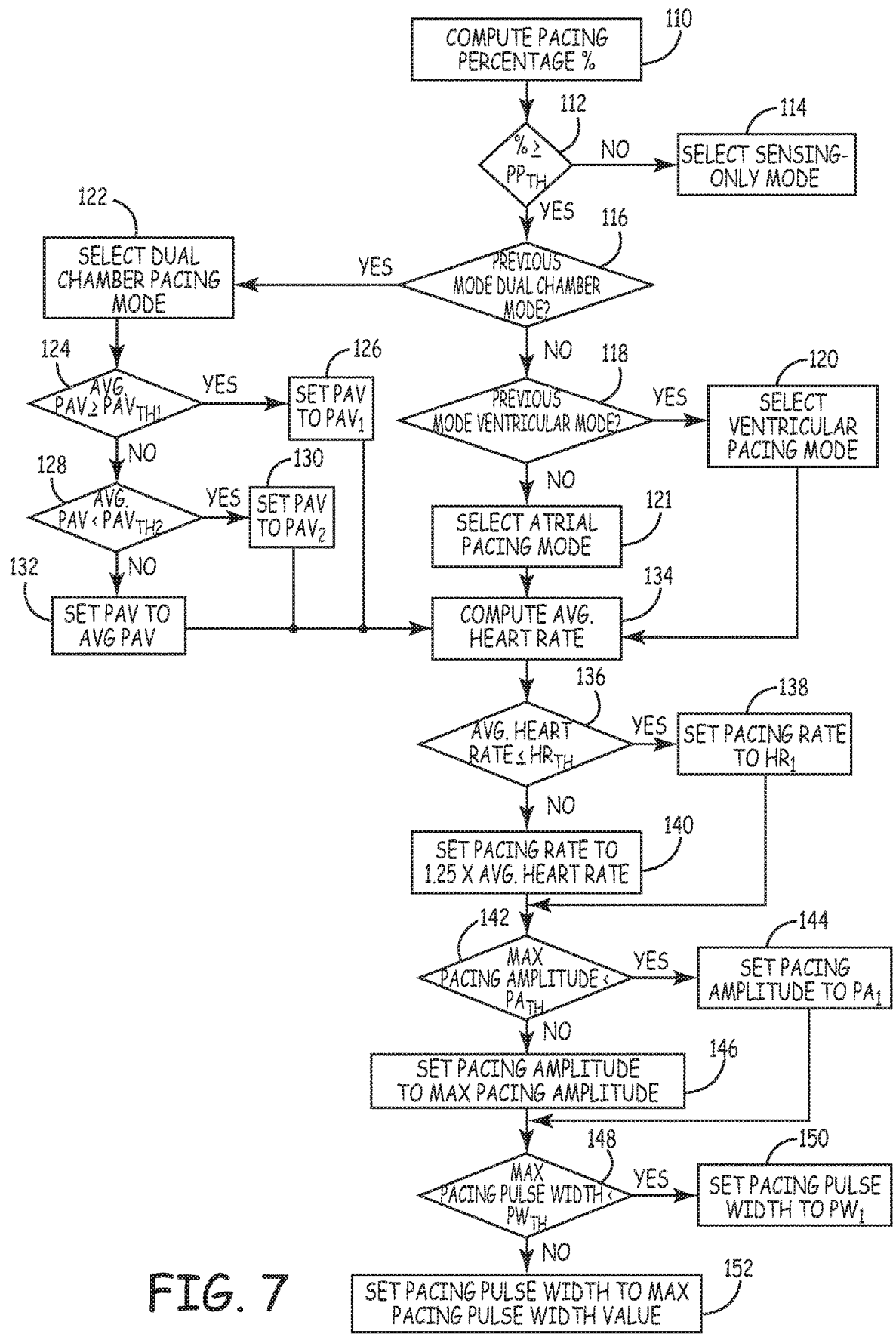
FIG. 7 is a flow diagram illustrating example operation of an IMD automatically determining parameters of the exposure operating mode in accordance with one aspect of this disclosure.

FIG. 7 is a flow diagram illustrating example operation of an IMD, such as IMD 14 or 32, automatically determining parameters of the exposure operating mode in accordance with one aspect of this disclosure. Processor 60 of IMD 32 computes a pacing percentage (%) over a predetermined period of time (e.g., 1-4 hours) (110). The pacing percentage may be computed by dividing the number of cardiac cycles during which a pacing pulse was delivered during the predetermined time by the total number of cardiac cycles during the predetermined period of time. Processor 60 compares the computed pacing percentage to a threshold pacing percentage ($PP_{TH}$) (112). If the pacing percentage is less than a threshold pacing percentage ("NO" branch of 112), processor 60 selects a sense-only operating mode as the exposure operating mode (114). Because there is no pacing in these operating modes, such operating modes may prevent processor 60 from delivering undesirable stimulation or withholding desirable stimulation.

If the pacing percentage is greater than or equal to the threshold pacing percentage ("YES" branch of 112), processor 60 analyzes the operating modes in which IMD 32 operated during the predetermined period of time to determine if IMD 32 operated in a dual-chamber pacing mode (116). If IMD 32 operated in any dual-chamber mode during the predetermined time period ("YES" branch of 116), processor 60 selects a dual-chamber pacing mode (122). The dual-chamber pacing mode may or may not include sensing, but is not responsive to the sensing.

When processor 60 selects a dual-chamber pacing mode, processor 60 may analyze PAV intervals during the predetermined period of time and select a PAV interval for the dual-chamber pacing mode based on the analysis. In the example illustrated in FIG. 7, processor 60 compares the average PAV interval during the predetermined time to a first PAV interval threshold ($PAV_{TH1}$) (124). When the average PAV interval is greater than or equal to the first PAV interval threshold ("YES" branch of 124), processor 60 sets the PAV interval for the exposure operating mode to a first predetermined PAV interval value ($PAV_1$) (126). When the average PAV interval is less than the first PAV interval threshold ("NO" branch of 124), processor 60 compares the average PAV interval during the predetermined time to a second PAV interval threshold ($PAV_{TH2}$) (128). When the average PAV interval is less than the second PAV interval threshold ("YES" branch of 128), processor 60 sets the PAV interval for the exposure operating mode to a second predetermined PAV interval value ($PAV_2$) (130). When the average PAV interval is greater than or equal to the second PAV interval threshold ("NO" branch of 128), processor 60 sets the PAV interval for the exposure operating mode to the average PAV interval during the predetermined period of time (132).

If IMD 32 has not operated in any dual-chamber mode during the predetermined time period ("NO" branch of 116), processor 60 determines whether IMD 32 operated in a ventricular-chamber pacing mode during the predetermined period of time (118). If IMD 32 operated in any ventricular-chamber pacing mode during the predetermined time period ("YES" branch of 118), processor 60 selects a ventricular-chamber pacing mode (120). If IMD 32 has not operated in any ventricular-chamber pacing mode during the predetermined time period ("NO" branch of 118), processor 60 selects an atrial-chamber pacing mode (121). The ventricular-chamber pacing mode or the atrial-chamber pacing mode may or may not include sensing, but are not responsive to the sensing.

Processor 60 may also determine one or more parameters of the selected pacing mode based on the stored information. In the example illustrated in FIG. 7, processor 60 computes an average heart rate over the predetermined period of time (134) and compares the average heart rate to a threshold heart rate ($HR_{TH}$) (136). When the average heart rate is less than or equal to the threshold heart rate ("YES" branch of 136), processor 60 sets the pacing rate for the selected pacing mode to a predetermined rate ($HR_1$) (e.g., 85 bpm) (138). When the average heart rate is greater than the threshold heart rate ("NO" branch of 136), processor 60 sets the pacing rate for the selected pacing mode to 1.25 times the average heart rate (140).

Processor 60 compares the highest pacing amplitude during the predetermined period of time to a threshold pacing amplitude ($PA_{TH}$) (142). When the highest pacing amplitude during the predetermined period of time is less than the threshold pacing amplitude ("YES" branch of 142), processor 60 sets the pacing amplitude for pacing pulses delivered during the exposure operating mode to a predetermined pacing amplitude ($PA_1$) (144). When the highest pacing amplitude during the predetermined period of time is greater than or equal to the threshold pacing amplitude ("NO" branch of 142), processor 60 sets the pacing amplitude for pacing pulses delivered during the exposure operating mode to the highest pacing amplitude that occurred during the predetermined period of time (146).

Processor 60 compares the highest pacing pulse width during the predetermined period of time to a threshold pacing pulse width ($PW_{TH}$) (148). When the highest pacing pulse width during the predetermined period of time is less than the threshold pacing pulse width ("YES" branch of 148), processor 60 sets the pacing pulse width for pacing pulses delivered during the exposure operating mode to a predetermined pacing pulse width ($PW_1$) (150). When the highest pacing pulse width during the predetermined period of time is greater than or equal to the threshold pacing pulse width ("NO" branch of 148), processor 60 sets the pacing pulse width for pacing pulses delivered during the exposure operating mode to the highest pacing pulse width that occurred during the predetermined period of time (152).

The example illustrated in FIG. 7 is for example purposes only. Processor 60 may automatically determine only a portion of the parameters discussed and/or additional, different parameters. Moreover, processor 60 may also perform other actions in the exposure operating mode. For example, IMD 32 may also suspend some functionality, e.g., diagnostic and counters, magnet mode, tachyarrhythmia and PVC detection, tachyarrhythmia therapies, or the like. Some example threshold values are provided in Table 1 above for purposes of illustration. Table 1 is for example purposes only and should not be considered limiting of the techniques as broadly described in this disclosure. The various thresholds and corresponding settings may be adjusted based on various considerations.

Figure 8:
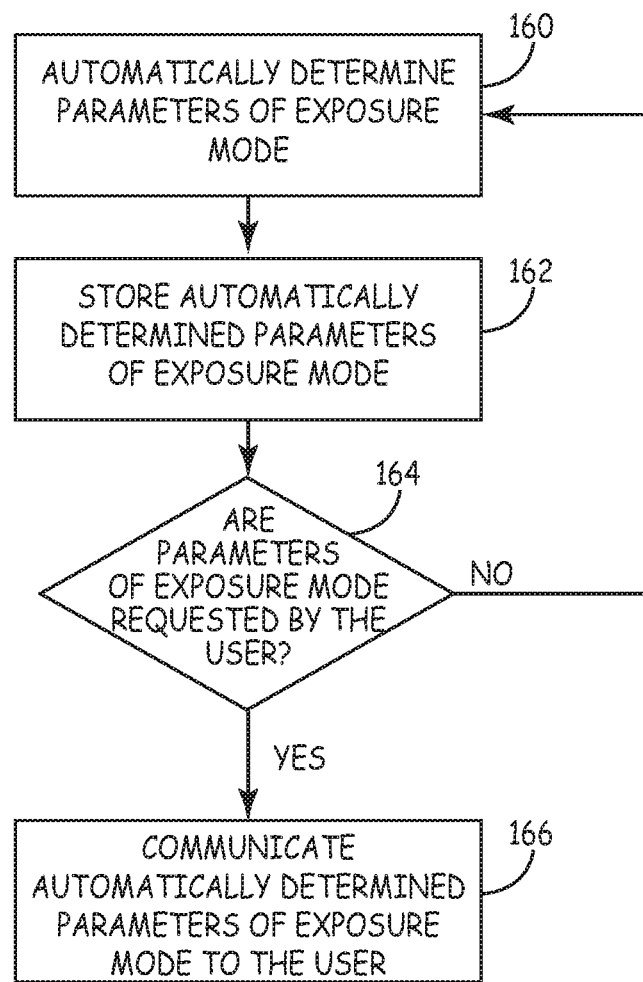
FIG. 8 is a flow diagram illustrating example operation of an IMD recommending parameters for the exposure operating mode to a user.

FIG. 8 is a flow diagram illustrating example operation of an IMD, such as IMD 14 or 32, recommending parameters for the exposure operating mode in accordance with one aspect of this disclosure. Processor 60 automatically determines at least a portion of the parameters and, in some instances all of the parameters, of the exposure operating mode (160). As described above, processor 60 may periodically determine the parameters of the exposure operating mode, e.g., every hour, two hours, four hours or the like. In automatically determining the parameters of the exposure operating mode, processor 60 may analyze any of a variety of stored information related to sensed physiological events and/or therapy provided over a predetermined period of time, including, but not limited to pacing modes in which the device operated, percentage of time during which therapy is provided, amplitudes of the therapy energy delivered, pulse widths of the therapy energy delivered, rate at which the therapy energy was delivered, average heart rate, peak heart rate, PAV intervals, pacing capture thresholds (e.g., rheobase and chronaxie), sensing amplitudes, arrhythmias or the like. Processor 60 stores the automatically determined parameters in memory 72 or other storage mechanism (162).

Processor 60 determines whether a user requests the automatically generated parameters (164). For example, a user may request the parameters by interacting with a programming device 18 to transmit a command requesting the automatically generated parameters. As another example, the user may interact with a remote device, e.g., computing device 26, to transmit the command over network 22 to IMD 32. When processor 60 determines that the parameters were not requested ("NO" branch of 164), processor 60 continues to automatically determine the parameters of the exposure operating mode. When processor 60 determines that the parameters were requested ("YES" branch of 164), processor 60 communicates the automatically determined parameters of the exposure operating mode to the user (166). Processor 60 may cause telemetry module 70 to transmit a communication to a programming device 18 that includes the parameters and programming device 18 may display the parameters to the user. In this manner, IMD 32 may recommend parameters of the exposure operating mode to a user, e.g., a physician.

The techniques described in this disclosure, including those attributed to IMD 14 and/or 32, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
automatically determining by a first device one or more parameters of an exposure operating mode by analyzing at least one of stored information that describes sensed physiological events or stored information that describes therapy provided over a predetermined period of time, the exposure operating mode for use by an implantable medical device during exposure of the implantable medical device to a disruptive energy field; and
providing by the first device the one or more automatically determined parameters to a user at the time of manual programming of the implantable medical device.

2. The method of claim 1, wherein
automatically determining the one or more parameters of the exposure operating mode comprises automatically determining, with the implantable medical device, the one or more parameters of the exposure operating mode; and
providing the one or more automatically determined parameters to the user comprises transmitting the one or more automatically determined parameters to an external device for presentation to the user.

3. The method of claim 1, wherein the stored information includes operating modes of a predetermined period of time and automatically determining the one or more parameters of the exposure operating mode comprises:
automatically determining one or more parameters of an exposure operating mode by analyzing pacing therapies provided during the predetermined period; and
selecting an operating mode to be used during the exposure mode based on the analysis.

4. The method of claim 1, wherein the stored information includes heart rates during a predetermined period of time and automatically determining the one or more parameters of the exposure operating mode comprises:
automatically determining one or more parameters of an exposure operating mode by analyzing the heart rates during the predetermined period of time; and
selecting a pacing rate of pacing pulses to be delivered during the exposure operating mode based on the analysis.

5. The method of claim 4, wherein selecting the pacing rate of pacing pulses to be delivered during the exposure operating mode based on the analysis comprises selecting a pacing rate that is higher than an average heart rate during the predetermined period.

6. The method of claim 5, wherein selecting the pacing rate that is higher than the average heart rate during the predetermined period comprises selecting a pacing rate that is a predetermined amount higher than the average heart rate.

7. The method of claim 6, wherein selecting the pacing rate that is a predetermined amount higher than the average heart rate comprises selecting a pacing rate that is at least twenty beats per minute higher than the average heart rate.

8. The method of claim 6, wherein selecting the pacing rate that is a predetermined amount higher than the average heart rate comprises selecting a pacing rate that is a predefined percentage higher than the average heart rate.

9. The method of claim 1, further comprising:
detecting presence of one or more energy fields generated by a magnetic resonance imaging (MM) device,
switching operation of the implantable medical device comprises switching from parameters of the current operating mode to the one or more automatically determined parameters of the exposure operating mode in response to detecting of the presence of the one or more energy fields generated by the MRI device.

10. The method of claim 1, wherein providing the one or more automatically determined parameters to the user comprises displaying the one or more automatically determined parameters to the user.

11. The method of claim 1, further comprising receiving, from the user, adjustments to the one or more automatically determined parameters.

12. The method of claim 1, wherein the stored information includes a pacing rate and the first device is configured to automatically determine the one or more parameters of the exposure operating mode based on a stored pacing rate.

13. A device comprising:
a memory;
a processor coupled to the memory, the processor configured to:
automatically determine one or more parameters of an exposure operating mode by analyzing at least one of stored information that is accessed from the memory and describes sensed physiological events or stored information that is accessed from the memory and describes parameters of therapy provided over a predetermined period of time, the exposure operating mode for use by an implantable medical device during exposure of the implantable medical device to a disruptive energy field; and
provide the one or more automatically determined parameters to a user at the time of manual programming of the implantable medical device.

14. The device of claim 13, wherein the device further comprises a telemetry module and the processor is configured to control to provide the one or more automatically determined parameters to the user by controlling the telemetry module to transmit the one or more automatically determined parameters to an external device for presentation to the user.

15. The device of claim 13, wherein the stored information includes operating modes of a predetermined period of time and the processor is configured to automatically determine the one or more parameters of the exposure operating mode by:
automatically determining one or more parameters of an exposure operating mode by analyzing pacing therapies provided during the predetermined period; and
selecting an operating mode to be used during the exposure mode based on the analysis.

16. The device of claim 13, wherein the stored information includes a pacing rate and the processor is configured to automatically determine the one or more parameters of the exposure operating mode based on a stored pacing rate.

17. The device of claim 13, wherein the stored information includes heart rates during a predetermined period of time and automatically determining the one or more parameters of the exposure operating mode comprises:
automatically determining one or more parameters of an exposure operating mode by analyzing the heart rates during the predetermined period of time; and
selecting a pacing rate of pacing pulses to be delivered during the exposure operating mode based on the analysis.

18. The device of claim 17, wherein selecting the pacing rate of pacing pulses to be delivered during the exposure operating mode based on the analysis comprises selecting a pacing rate that is higher than an average heart rate during the predetermined period.

19. The method of claim 18, wherein selecting the pacing rate that is higher than the average heart rate during the predetermined period comprises selecting a pacing rate that is a predetermined amount higher than the average heart rate.

20. The method of claim 19, wherein selecting the pacing rate that is a predetermined amount higher than the average heart rate comprises selecting a pacing rate that is at least twenty beats per minute higher than the average heart rate.

21. The method of claim 19, wherein selecting the pacing rate that is a predetermined amount higher than the average heart rate comprises selecting a pacing rate that is a predefined percentage higher than the average heart rate.

22. The device of claim 13, further comprising:
detecting presence of one or more energy fields generated by a magnetic resonance imaging (MM) device,
switching operation of the implantable medical device comprises switching from parameters of the current operating mode to the one or more automatically determined parameters of the exposure operating mode in response to detecting of the presence of the one or more energy fields generated by the MRI device.

23. The device of claim 13, wherein providing the one or more automatically determined parameters to the user comprises displaying the one or more automatically determined parameters to the user.

24. The device of claim 13, further comprising receiving, from the user via a user interface, adjustments to the one or more automatically determined parameters.

* * * * *